US010481503B2

(12) United States Patent
Van Der Schaar et al.

(10) Patent No.: US 10,481,503 B2
(45) Date of Patent: Nov. 19, 2019

(54) METHOD AND APPARATUS FOR MEASURING A PARAMETER OF A LITHOGRAPHIC PROCESS, SUBSTRATE AND PATTERNING DEVICES FOR USE IN THE METHOD

(71) Applicant: ASML Netherlands B.V., Veldhoven (NL)

(72) Inventors: Maurits Van Der Schaar, Eindhoven (NL); Youping Zhang, San Jose, CA (US); Hendrik Jan Hidde Smilde, Veldhoven (NL); Anagnostis Tsiatmas, Eindhoven (NL); Adriaan Johan Van Leest, Eindhoven (NL); Alok Verma, Eindhoven (NL); Thomas Theeuwes, Veldhoven (NL); Hugo Augustinus Joseph Cramer, Eindhoven (NL); Paul Christiaan Hinnen, Veldhoven (NL)

(73) Assignee: ASML Netherlands B.V., Veldhoven (NL)

( * ) Notice: Subject to any disclaimer, the term of this patent is extended or adjusted under 35 U.S.C. 154(b) by 0 days.

(21) Appl. No.: 15/237,246

(22) Filed: Aug. 15, 2016

(65) Prior Publication Data
US 2017/0059999 A1 Mar. 2, 2017

Related U.S. Application Data

(60) Provisional application No. 62/301,880, filed on Mar. 1, 2016, provisional application No. 62/210,938, filed on Aug. 27, 2015.

(51) Int. Cl.
*G03F 7/20* (2006.01)
*G01N 21/95* (2006.01)
*G01N 21/47* (2006.01)

(52) U.S. Cl.
CPC .......... *G03F 7/70491* (2013.01); *G01N 21/47* (2013.01); *G01N 21/9501* (2013.01); *G03F 7/70633* (2013.01); *G03F 7/70683* (2013.01)

(58) Field of Classification Search
CPC ................ G01N 21/47; G01N 21/9501; G03F 7/70683; G03F 7/70625
(Continued)

(56) References Cited

U.S. PATENT DOCUMENTS 7,460,237 B1 * 12/2008 Cramer ............... G03F 7/70625
355/55
7,791,727 B2 9/2010 Den Boef et al.
(Continued)

FOREIGN PATENT DOCUMENTS

CN 1916603 A 2/2007
JP 2014-512101 A 5/2014
(Continued)

OTHER PUBLICATIONS

International Search Report and Written Opinion of the International Searching Authority, directed to related International Patent Application No. PCT/EP2016/069790, dated Dec. 6, 2016; 10 pages.
(Continued)

*Primary Examiner* — Isiaka O Akanbi
(74) *Attorney, Agent, or Firm* — Sterne, Kessler, Goldstein & Fox P.L.L.C.

(57) ABSTRACT

A substrate has first and second target structures formed by a lithographic process. Each target structure has a two-dimensional periodic structure formed in a single layer using first and second lithographic steps. The first target structure has features defined in the second lithographic step displaced relative to features defined in the first lithographic step by a first bias amount. The second target structure has
(Continued)

features defined in the second lithographic step displaced relative to features defined in the first lithographic step by a second bias amount. An angle-resolved scatter spectrum of the first target structure and an angle-resolved scatter spectrum of the second target structure is obtained. A measurement of a parameter of a lithographic process is derived from the measurements using asymmetry found in the scatter spectra of the first and second target structures.

16 Claims, 9 Drawing Sheets

(58) Field of Classification Search
USPC .................. 356/601–614, 401, 400, 492
See application file for complete search history.

(56) References Cited

U.S. PATENT DOCUMENTS

| | | | |
|---|---|---|---|
| 7,791,732 B2 | 9/2010 | Den Boef et al. | |
| 7,911,612 B2* | 3/2011 | Kiers | G01N 21/4788 356/399 |
| 8,339,595 B2 | 12/2012 | Den Boef | |
| 8,411,287 B2 | 4/2013 | Smilde et al. | |
| 8,705,007 B2 | 4/2014 | Cramer et al. | |
| 8,760,662 B2 | 6/2014 | Den Boef et al. | |
| 8,867,020 B2 | 10/2014 | Smilde et al. | |
| 8,918,746 B1* | 12/2014 | Yuan | G06F 17/50 250/492.22 |
| 9,081,303 B2 | 7/2015 | Cramer et al. | |
| 9,110,385 B2 | 8/2015 | Den Boef | |
| 9,735,029 B1* | 8/2017 | Chu | H01L 27/0207 |
| 2003/0206298 A1 | 11/2003 | Bischoff et al. | |
| 2003/0212525 A1 | 11/2003 | Bischoff et al. | |
| 2005/0195398 A1* | 9/2005 | Adel | B82Y 10/00 356/401 |
| 2006/0033921 A1 | 2/2006 | Den Boef et al. | |
| 2006/0066855 A1* | 3/2006 | Boef | G03F 7/70341 356/401 |
| 2008/0050040 A1* | 2/2008 | Geers | G03F 7/70425 382/291 |
| 2009/0087756 A1 | 4/2009 | Schulz | |
| 2009/0168062 A1* | 7/2009 | Straaijer | G03F 7/70566 356/364 |
| 2009/0224413 A1 | 9/2009 | Ghinovker | |
| 2010/0007863 A1 | 1/2010 | Jordanoska | |
| 2010/0165312 A1* | 7/2010 | Megens | G03B 27/42 355/53 |
| 2010/0201963 A1 | 8/2010 | Cramer et al. | |
| 2010/0328655 A1 | 12/2010 | Den Boef | |
| 2011/0027704 A1 | 2/2011 | Cramer et al. | |
| 2011/0043791 A1 | 2/2011 | Smilde et al. | |
| 2011/0069292 A1 | 3/2011 | Den Boef | |
| 2011/0073775 A1 | 3/2011 | Setija et al. | |
| 2011/0188020 A1 | 8/2011 | Den Boef | |
| 2012/0120396 A1 | 5/2012 | Kandel et al. | |
| 2012/0123581 A1* | 5/2012 | Smilde | G03F 7/70483 700/105 |
| 2012/0242970 A1 | 9/2012 | Smilde et al. | |
| 2013/0035888 A1 | 2/2013 | Kandel et al. | |
| 2013/0135600 A1 | 5/2013 | Middlebrooks et al. | |
| 2013/0258310 A1* | 10/2013 | Smilde | G03F 7/70633 355/77 |
| 2014/0019097 A1 | 1/2014 | Bakeman et al. | |
| 2014/0339284 A1 | 11/2014 | Straat | |
| 2015/0185625 A1 | 7/2015 | Chen et al. | |
| 2016/0146740 A1 | 5/2016 | Lu et al. | |
| 2016/0161863 A1* | 6/2016 | Den Boef | G01B 11/24 355/67 |
| 2017/0011929 A1* | 1/2017 | Jun | H01L 21/3086 |
| 2017/0059999 A1 | 3/2017 | Van Der Schaar et al. | |
| 2017/0255112 A1 | 9/2017 | Van Leest et al. | |
| 2017/0255736 A1 | 9/2017 | Van Leest et al. | |
| 2017/0255737 A1 | 9/2017 | Van Leest et al. | |
| 2017/0255738 A1 | 9/2017 | Van Leest et al. | |
| 2017/0256465 A1 | 9/2017 | Van Leest et al. | |

FOREIGN PATENT DOCUMENTS

| | | |
|---|---|---|
| JP | 2014-526402 A | 10/2014 |
| WO | WO 2009/078708 A1 | 6/2009 |
| WO | WO 2009/100867 A1 | 8/2009 |
| WO | WO 2009/106279 A1 | 9/2009 |
| WO | WO 2010/034674 A1 | 4/2010 |
| WO | WO 2011/151121 A1 | 12/2011 |
| WO | WO 2014/062972 A1 | 4/2014 |
| WO | WO 2015/009619 A1 | 1/2015 |
| WO | WO 2015062854 | 5/2015 |
| WO | WO 2015/082158 A1 | 6/2015 |
| WO | WO 2015/090838 A1 | 6/2015 |
| WO | WO 2015078669 | 6/2015 |
| WO | WO 2016134954 | 9/2016 |

OTHER PUBLICATIONS

Leray et al., "Overlay Metrology for Double Patterning Processes," Metrology, Inspection, and Process Control for Microlithography XXIII, SPIE, vol. 7272, 2009; pp. 72720G-1-2720G-9.

Bencher C., "Multiple Patterning for Immersion Extension and EUV Insertion," Applied Materials CTO Group, pp. 1-31.

International Search Report and Written Opinion of the International Searching Authority directed to related International Application No. PCT/EP2017/054719, dated May 9, 2017; 12 pages.

International Search Report and Written Opinion of the International Searching Authority directed to related International Application No. PCT/EP2017/054748, dated Jun. 13, 2016; 9 pages.

International Search Report and Written Opinion of the International Searching Authority directed to related International Application. No. PCT/EP2017/054714, dated Apr. 24, 2017; 11 pages.

International Search Report and Written Opinion of the International Searching Authority directed to related international Application No. PCT/EP2017/054761, dated Jun. 3, 2016; 14 pages.

International Search Report and Written Opinion of the International Searching Authority directed to related International Application No. PCT/EP2017/054737, dated May 9, 2017; 12 pages.

International Preliminary Report on Patentability and Written Opinion of the International Searching Authority directed to related International Patent Application No. PCT/EP2016/069790, dated Feb. 27, 2018; 6 pages.

Office Action and Search Report directed to related Chinese Patent Application No. 201680049910.6, dated Jul. 27, 2019, with attached English-language translation; 14 pages.

* cited by examiner

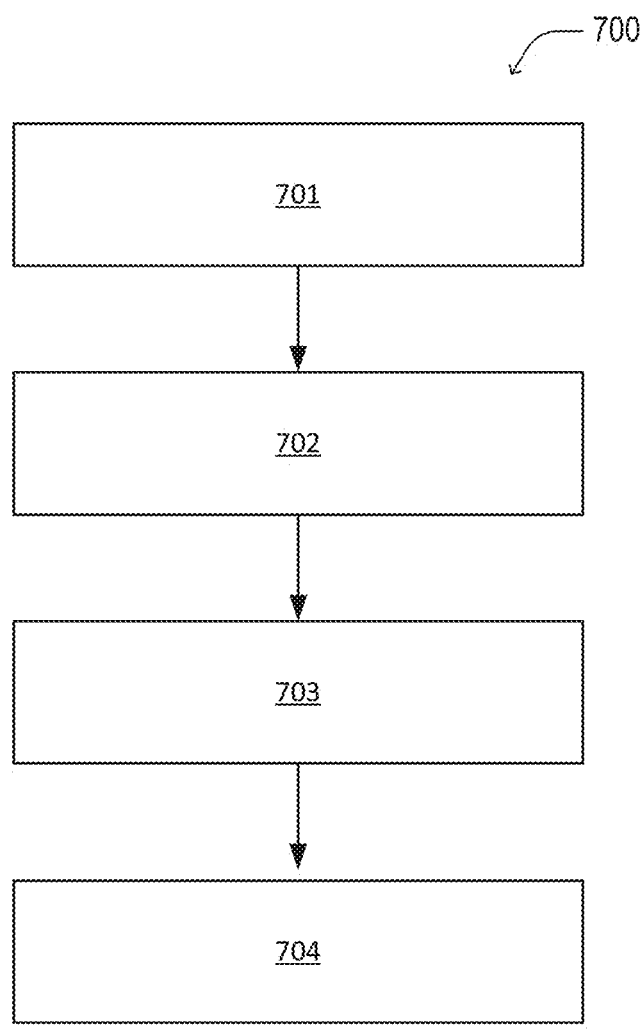

METHOD AND APPARATUS FOR MEASURING A PARAMETER OF A LITHOGRAPHIC PROCESS, SUBSTRATE AND PATTERNING DEVICES FOR USE IN THE METHOD

CROSS REFERENCE TO RELATED APPLICATIONS

This application claims benefit under 35 U.S.C § 119(e) to U.S. Provisional Applications 62/210,938 and 62/301,880, which are all incorporated by reference herein in their entireties.

BACKGROUND

Field of the Invention

The present invention relates to methods of manufacture of products such as semiconductor devices using lithographic techniques.

Background Art

A lithographic apparatus is a machine that applies a desired pattern onto a substrate, usually onto a target portion of the substrate. A lithographic apparatus can be used, for example, in the manufacture of integrated circuits (ICs). In that instance, a patterning device, which is alternatively referred to as a mask or a reticle, may be used to generate a circuit pattern to be formed on an individual layer of the IC. This pattern can be transferred onto a target portion (e.g., including part of, one, or several dies) on a substrate (e.g., a silicon wafer). Multiple layers, each having a particular pattern and material composition, are applied to define functional devices and interconnections of the finished product.

Current and next generation processes often rely on so-called multiple patterning techniques to produce device features having dimensions far smaller than can be printed directly by the lithographic apparatus. Multiple patterning steps, each having its own mask or reticle, are performed to define a desired device pattern in a single layer on the substrate. Many different examples of multiple patterning are known. In some processes, a regular, grid structure is formed as a basis for the desired device pattern. Then using a circuit-specific mask pattern, lines that form the grid structure are cut at specific locations to separate the lines into individual segments. The grid structure may be exceptionally fine in dimensions, with a pitch in the tens or even teens of nanometers.

In a lithographic process, it is desirable frequently to make measurements of structures created, e.g., for process control and verification. Various tools for making such measurements are known, including scanning electron microscopes, which are often used to measure critical dimension (CD), and specialized tools to measure overlay, the accuracy of alignment of two layers of a substrate. Final performance of manufactured device depends critically on the accuracy of positioning and dimensioning of the cut mask relative to the grid structure. (The cut mask in this context is what defines the circuit-specific locations at which the grid structure is modified to form functional circuits.) Overlay error may cause cutting or other modification to occur in a wrong place. Dimensional (CD) errors may cause cuts be too large, or too small (in an extreme case, cutting a neighboring grid line by mistake, or failing to cut the intended grid line completely).

Other performance parameters of the lithographic process may be also of interest, for example in optical lithography parameters of focus and exposure dose may also require measuring.

However, the dimensions of modern product structures are so small that they cannot be imaged by optical metrology techniques. Small features include for example those formed by multiple patterning processes, and pitch-multiplication. (These terms are explained further below.) In effect, the structures are too small for traditional metrology techniques which cannot "see" them. Hence, targets used for high-volume metrology often use features that are much larger than the products whose overlay errors or critical dimensions are the property of interest.

While scanning electron microscopes are able to resolve modern products structures, measurements performed with scanning electron microscopes are much more time consuming, as well as more expensive, than optical measurements.

SUMMARY

The inventors have recognized that it is possible to perform metrology measurements on structures with dimensions and processing similar to product structures, by using zeroth order light scattered by these structures.

In a first aspect of the invention, there is provided a method of measuring a parameter of a lithographic process, the lithographic process being for forming a two-dimensional, periodic product structure in a single material layer using two or more lithographic steps, the method comprising: providing first and second target structures, each target structure comprising a two-dimensional periodic structure formed in a single material layer on a substrate using first and second lithographic steps, wherein, in the first target structure, features defined in the second lithographic step are displaced relative to features defined in the first lithographic step by a first bias amount that is close to one half of a spatial period of the features formed in the first lithographic step, and, in the second target structure, features defined in the second lithographic step are displaced relative to features defined in the first lithographic step by a second bias amount close to one half of said spatial period and different to the first bias amount; obtaining an angle-resolved scatter spectrum of the first target structure and an angle-resolved scatter spectrum of the second target structure; and deriving a measurement of said parameter using asymmetry found in the scatter spectrum of the first target structure and asymmetry found in the scatter spectrum of the second target structure.

In some embodiments, obtaining the angle-resolved scatter spectrum of each target structure comprises: illuminating the target structure with radiation; and detecting the angle-resolved scatter spectrum using zero order radiation scattered by the target structure.

The spatial period of each target structure is significantly shorter than a wavelength of the radiation used to illuminate the target structures.

The method may further comprise selecting the wavelength of radiation from a range of available wavelengths so as to optimize strength and linearity of asymmetry in the angle-resolved scatter spectra of the target structures.

In some embodiments, the step of deriving said parameter comprises calculating a measurement of overlay error relating to said product structures using the asymmetry found in the scatter spectrum of the first target structure, the asymmetry found in the scatter spectrum of the second target structure and knowledge of the first bias amount and the second bias amount.

Features of the target structures that are defined in the first lithographic step may comprise a grid structure defining said spatial period in a first direction, and features of said target structures that are defined in the second lithographic step may comprise modifications of the grid structure at locations spaced periodically in a two-dimensional periodic arrangement.

The features of said target structures that are defined in the first lithographic step may further comprise a grid structure defining said spatial period in a first direction, and features of said target structures that are defined in the second lithographic step may further comprise cuts in elements of the grid structure.

In some embodiments, the first target structure and the second target structure may be formed by etching and/or deposition processes after the first and second lithographic steps have been used to define their features In some embodiments, a product structure may be formed in the same material layer elsewhere on the same substrate using said first and second lithographic steps, wherein, in the product structure, features defined in the second lithographic step are not displaced relative to features defined in the first lithographic step by any bias amount.

The invention further provides a substrate for use in measuring a parameter of a lithographic process, the substrate comprising first and second target structures, each target structure comprising a two-dimensional periodic structure formed in a single material layer using said first and second lithographic steps, wherein, in the first target structure, features defined in the second lithographic step are displaced relative to features defined in the first lithographic step by a first bias amount that is close to one half of a spatial period of the features formed in the first lithographic step, and, in the second target structure, features defined in the second lithographic step are displaced relative to features defined in the first lithographic step by a second bias amount that is close to one half of said spatial period and different to the first bias amount.

The invention yet further provides a metrology apparatus for use in a method according to the invention as set forth above.

In some embodiments, the metrology apparatus may comprise: a support for a substrate on which a first target structure and a second target structure have been formed; an optical system for selectively illuminating each target structure with radiation and collecting at least zero order radiation scattered by the target structure; a detector for detecting an angle-resolved scatter spectrum of each using said zero order radiation; and a processor arranged to derive a parameter of a lithographic process using asymmetry of the angle-resolved scatter spectrum of the first target structure and asymmetry of the angle-resolved scatter spectrum of the second target structure.

The invention yet further provides a lithographic system comprising: a lithographic apparatus for use in a lithographic process; and a metrology apparatus according to the invention as set forth above for use in measuring a parameter of the lithographic process using first and second target structures formed at least partially using the lithographic apparatus.

The invention yet further provides a computer program product comprising machine readable instructions which, when run on a suitable processor, cause the processor to perform the deriving step of the method according to the invention as set forth above.

The invention yet further provides a method to determine an overlay error on a substrate on which product structures have been formed, the product structures including first product features that have been defined by a first lithographic process and second product features that have been defined by a second lithographic process, the overlay error comprising a positional deviation between the first product features and the second product features, the method comprising: providing a first target structure on the substrate, the first target structure comprising first target features defined by the first lithographic process and second target features defined by the second lithographic step, a positional relationship between the first target features and the second target features depending on a first bias value and the overlay error; and providing a second target structure on the substrate, the second target structure comprising third target features defined by the first lithographic process and fourth target features defined by the second lithographic step, a positional relationship between the third target features and the fourth target features depending on a second bias value and the overlay error; detecting a first angle-resolved scatter spectrum using zero order radiation diffracted from the first target structure; detecting a second angle-resolved scatter spectrum using zero order radiation diffracted from the second target structure; calculating a measurement of the overlay error based on asymmetry observed in the first angle-resolved scatter spectrum and the second angle-resolved scatter spectrum and on knowledge of the first bias value and the second bias value.

Further aspects, features and advantages of the invention, as well as the structure and operation of various embodiments of the invention, are described in detail below with reference to the accompanying drawings. It is noted that the invention is not limited to the specific embodiments described herein. Such embodiments are presented herein for illustrative purposes only. Additional embodiments will be apparent to persons skilled in the relevant art(s) based on the teachings contained herein.

BRIEF DESCRIPTION OF THE DRAWINGS

Embodiments of the invention will now be described, by way of example, with reference to the accompanying drawings in which:

FIG. 7 is a flowchart of a method for measuring a parameter of a lithographic process according to an embodiment of the present invention;

DETAILED DESCRIPTION

Before describing embodiments of the invention in detail, it is instructive to present an example environment in which embodiments of the present invention may be implemented.

Figure 1:
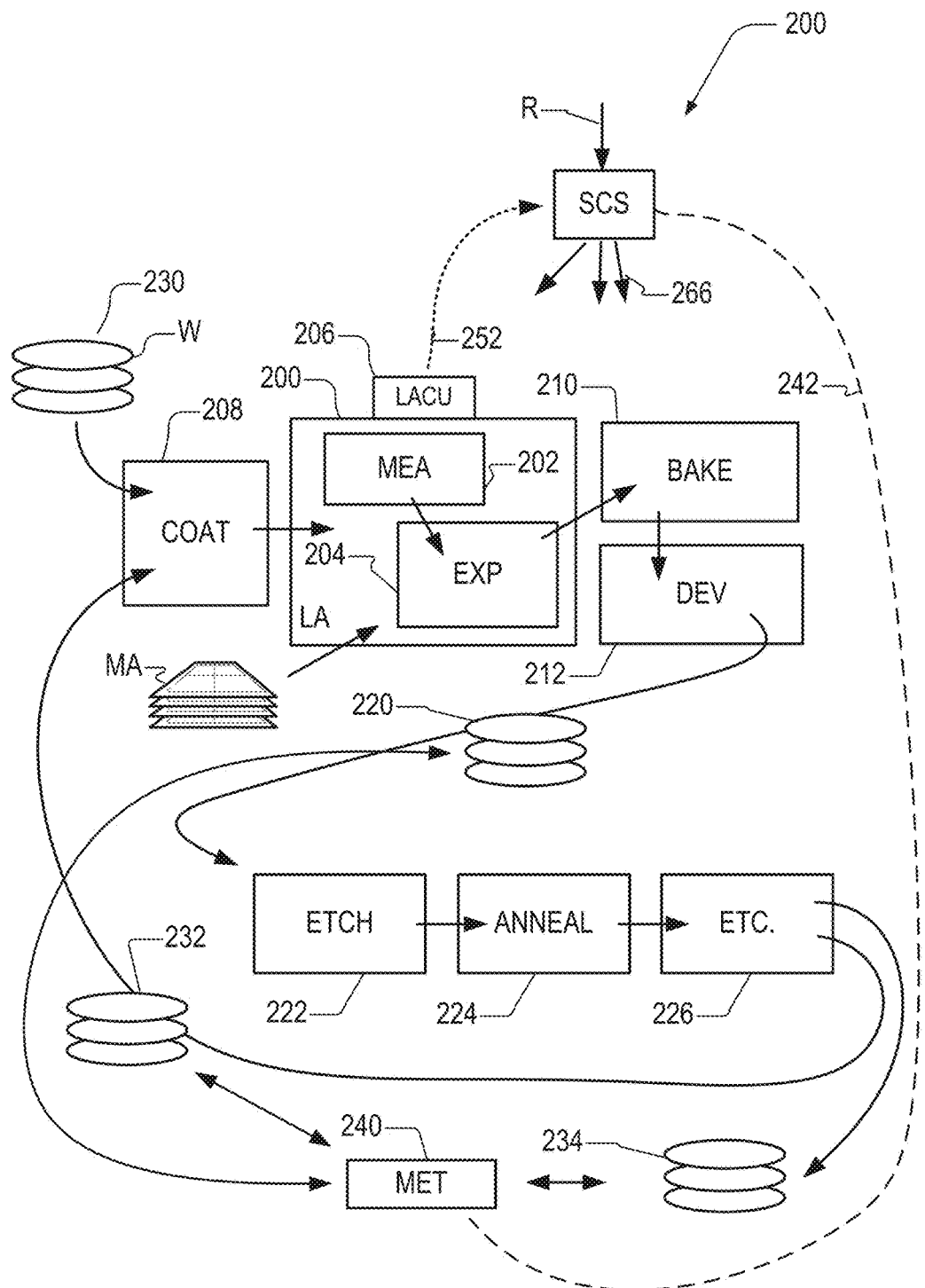
FIG. 1 depicts a lithographic apparatus together with other apparatuses forming a production facility for semiconductor devices.

FIG. 1 at 200 shows a lithographic apparatus LA as part of an industrial production facility implementing a high-volume, lithographic manufacturing process. In the present example, the manufacturing process is adapted for the manufacture of for semiconductor products (integrated circuits) on substrates such as semiconductor wafers. The skilled person will appreciate that a wide variety of products can be manufactured by processing different types of substrates in variants of this process. The production of semiconductor products is used purely as an example which has great commercial significance today.

Within the lithographic apparatus (or "litho tool" 200 for short), a measurement station MEA is shown at 202 and an exposure station EXP is shown at 204. A control unit LACU is shown at 206. In this example, each substrate visits the measurement station and the exposure station to have a pattern applied. In an optical lithographic apparatus, for example, a projection system is used to transfer a product pattern from a patterning device MA onto the substrate using conditioned radiation and a projection system. This is done by forming an image of the pattern in a layer of radiation-sensitive resist material.

The term "projection system" used herein should be broadly interpreted as encompassing any type of projection system, including refractive, reflective, catadioptric, magnetic, electromagnetic and electrostatic optical systems, or any combination thereof, as appropriate for the exposure radiation being used, or for other factors such as the use of an immersion liquid or the use of a vacuum. The patterning MA device may be a mask or reticle, which imparts a pattern to a radiation beam transmitted or reflected by the patterning device. Well-known modes of operation include a stepping mode and a scanning mode. As is well known, the projection system may cooperate with support and positioning systems for the substrate and the patterning device in a variety of ways to apply a desired pattern to many target portions across a substrate. Programmable patterning devices may be used instead of reticles having a fixed pattern. The radiation for example may include electromagnetic radiation in the deep ultraviolet (DUV) or extreme ultraviolet (EUV) wavebands. The present disclosure is also applicable to other types of lithographic process, for example imprint lithography and direct writing lithography, for example by electron beam.

The lithographic apparatus control unit LACU which controls all the movements and measurements of various actuators and sensors to receive substrates W and reticles MA and to implement the patterning operations. LACU also includes signal processing and data processing capacity to implement desired calculations relevant to the operation of the apparatus. In practice, control unit LACU will be realized as a system of many sub-units, each handling the real-time data acquisition, processing and control of a subsystem or component within the apparatus.

Before the pattern is applied to a substrate at the exposure station EXP, the substrate is processed in at the measurement station MEA so that various preparatory steps may be carried out. The preparatory steps may include mapping the surface height of the substrate using a level sensor and measuring the position of alignment marks on the substrate using an alignment sensor. The alignment marks are arranged nominally in a regular grid pattern. However, due to inaccuracies in creating the marks and also due to deformations of the substrate that occur throughout its processing, the marks deviate from the ideal grid. Consequently, in addition to measuring position and orientation of the substrate, the alignment sensor in practice must measure in detail the positions of many marks across the substrate area, if the apparatus is to print product features at the correct locations with very high accuracy. The apparatus may be of a so-called dual stage type which has two substrate tables, each with a positioning system controlled by the control unit LACU. While one substrate on one substrate table is being exposed at the exposure station EXP, another substrate can be loaded onto the other substrate table at the measurement station MEA so that various preparatory steps may be carried out. The measurement of alignment marks is therefore very time-consuming and the provision of two substrate tables enables a substantial increase in the throughput of the apparatus. If the position sensor IF is not capable of measuring the position of the substrate table while it is at the measurement station as well as at the exposure station, a second position sensor may be provided to enable the positions of the substrate table to be tracked at both stations. Lithographic apparatus LA may for example is of a so-called dual stage type which has two substrate tables and two stations—an exposure station and a measurement station—between which the substrate tables can be exchanged.

Within the production facility, apparatus 200 forms part of a "litho cell" or "litho cluster" that contains also a coating apparatus 208 for applying photosensitive resist and other coatings to substrates W for patterning by the apparatus 200. At an output side of apparatus 200, a baking apparatus 210 and developing apparatus 212 are provided for developing the exposed pattern into a physical resist pattern. Between all of these apparatuses, substrate handling systems take care of supporting the substrates and transferring them from one piece of apparatus to the next. These apparatuses, which are often collectively referred to as the track, are under the control of a track control unit which is itself controlled by a supervisory control system SCS, which also controls the lithographic apparatus via lithographic apparatus control unit LACU. Thus, the different apparatus can be operated to maximize throughput and processing efficiency. Supervisory control system SCS receives recipe information R which provides in great detail a definition of the steps to be performed to create each patterned substrate.

Once the pattern has been applied and developed in the litho cell, patterned substrates 220 are transferred to other processing apparatuses such as are illustrated at 222, 224, 226. A wide range of processing steps is implemented by various apparatuses in a typical manufacturing facility. For the sake of example, apparatus 222 in this embodiment is an etching station, and apparatus 224 performs a post-etch annealing step. Further physical and/or chemical processing steps are applied in further apparatuses, 226, etc. Numerous types of operation can be required to make a real device, such as deposition of material, modification of surface material characteristics (oxidation, doping, ion implantation etc.), chemical-mechanical polishing (CMP), and so forth. The apparatus 226 may, in practice, represent a series of different processing steps performed in one or more apparatuses. As another example, apparatus and processing steps may be provided for the implementation of self-aligned multiple patterning, to produce multiple smaller features based on a precursor pattern laid down by the lithographic apparatus.

As is well known, the manufacture of semiconductor devices involves many repetitions of such processing, to build up device structures with appropriate materials and patterns, layer-by-layer on the substrate. Accordingly, substrates 230 arriving at the litho cluster may be newly prepared substrates, or they may be substrates that have been processed previously in this cluster or in another apparatus entirely. Similarly, depending on the required processing, substrates 232 on leaving apparatus 226 may be returned for a subsequent patterning operation in the same litho cluster, they may be destined for patterning operations in a different cluster, or they may be finished products to be sent for dicing and packaging.

Each layer of the product structure requires a different set of process steps, and the apparatuses 226 used at each layer may be completely different in type. Further, even where the processing steps to be applied by the apparatus 226 are nominally the same, in a large facility, there may be several supposedly identical machines working in parallel to perform the step 226 on different substrates. Small differences in set-up or faults between these machines can mean that they influence different substrates in different ways. Even steps that are relatively common to each layer, such as etching (apparatus 222) may be implemented by several etching apparatuses that are nominally identical but working in parallel to maximize throughput. In practice, moreover, different layers require different etch processes, for example chemical etches, plasma etches, according to the details of the material to be etched, and special requirements such as, for example, anisotropic etching.

The previous and/or subsequent processes may be performed in other lithography apparatuses, as just mentioned, and may even be performed in different types of lithography apparatus. For example, some layers in the device manufacturing process which are very demanding in parameters such as resolution and overlay may be performed in a more advanced lithography tool than other layers that are less demanding. Therefore some layers may be exposed in an immersion type lithography tool, while others are exposed in a 'dry' tool. Some layers may be exposed in a tool working at DUV wavelengths, while others are exposed using EUV wavelength radiation.

In order that the substrates that are exposed by the lithographic apparatus are exposed correctly and consistently, it is desirable to inspect exposed substrates to measure properties such as overlay errors between subsequent layers, line thicknesses, critical dimensions (CD), etc. Accordingly a manufacturing facility in which litho cell LC is located also includes metrology system which receives some or all of the substrates W that have been processed in the litho cell. Metrology results are provided directly or indirectly to the supervisory control system SCS. If errors are detected, adjustments may be made to exposures of subsequent substrates, especially if the metrology can be done soon and fast enough that other substrates of the same batch are still to be exposed. Also, already exposed substrates may be stripped and reworked to improve yield, or discarded, thereby avoiding performing further processing on substrates that are known to be faulty. In a case where only some target portions of a substrate are faulty, further exposures can be performed only on those target portions which are good.

Also shown in FIG. 1 is a metrology apparatus 240 which is provided for making measurements of parameters of the products at desired stages in the manufacturing process. A common example of a metrology station in a modern lithographic production facility is a scatterometer, for example an angle-resolved scatterometer or a spectroscopic scatterometer, and it may be applied to measure properties of the developed substrates at 220 prior to etching in the apparatus 222. Using metrology apparatus 240, it may be determined, for example, that important performance parameters such as overlay or critical dimension (CD) do not meet specified accuracy requirements in the developed resist. Prior to the etching step, the opportunity exists to strip the developed resist and reprocess the substrates 220 through the litho cluster. The metrology results 242 from the apparatus 240 can be used to maintain accurate performance of the patterning operations in the litho cluster, by supervisory control system SCS and/or control unit LACU 206 making small adjustments over time, thereby minimizing the risk of products being made out-of-specification, and requiring re-work.

Additionally, metrology apparatus 240 and/or other metrology apparatuses (not shown) can be applied to measure properties of the processed substrates 232, 234, and incoming substrates 230. The metrology apparatus can be used on the processed substrate to determine important parameters such as overlay or CD. In accordance with embodiments of the present disclosure, the metrology apparatus is used to measure properties of structures having the same material and dimensions as functional product structures, which have been formed using one or more lithographic steps, etching and other processes after lithographic exposure.

Figure 2:
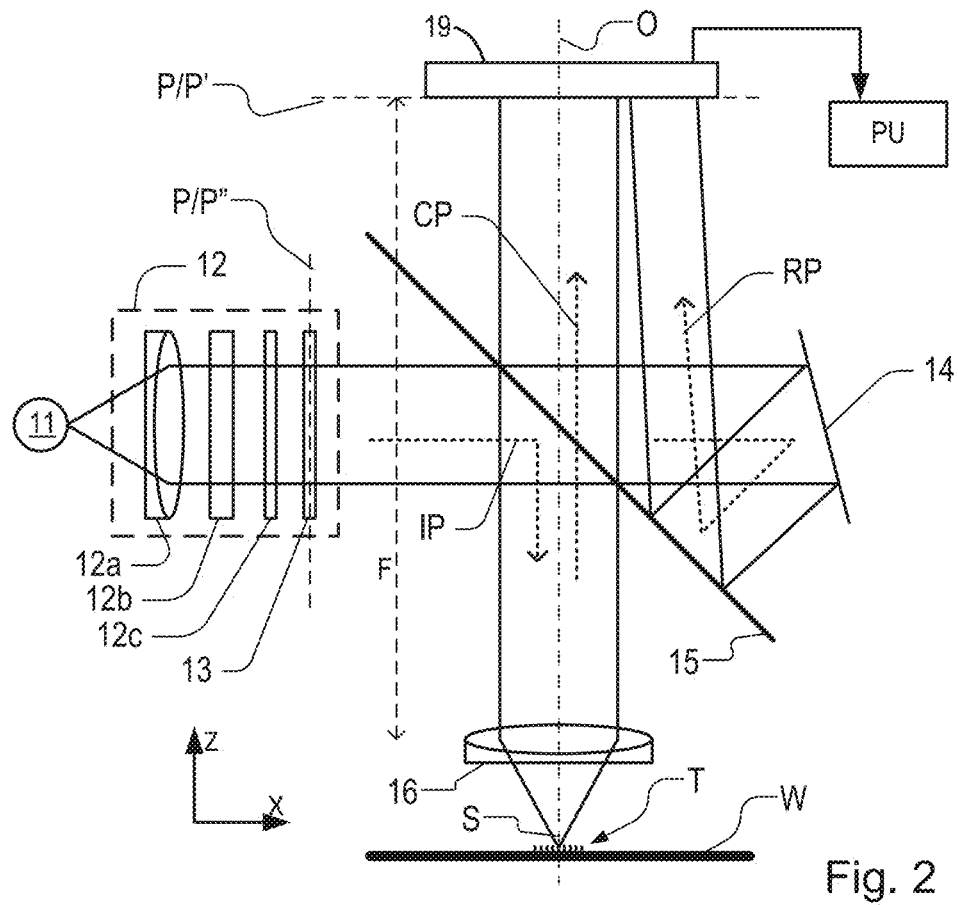
FIG. 2 depicts a scatterometer configured to capture an angle-resolved scatter spectrum according to an embodiment of the present invention.

FIG. 2 shows the basic elements of a known angle-resolved scatterometer that may be used as a metrology apparatus in embodiments of the present disclosure. In this type of metrology apparatus, radiation emitted by a radiation source 11 is conditioned by an illumination system 12. For example, illumination system 12 may include a collimating using lens system 12a, a color filter 12b, a polarizer 12c and an aperture device 13. The conditioned radiation follows an illumination path IP, in which it is reflected by partially reflecting surface 15 and focused into a spot S on substrate W via a microscope objective lens 16. A metrology target T may be formed on substrate W. Lens 16, has a high numerical aperture (NA), for example at least 0.9 or at least 0.95. Immersion fluid can be used to obtain with numerical apertures greater than 1, if desired.

As in the lithographic apparatus LA, one or more substrate tables may be provided to hold the substrate W during measurement. Coarse and fine positioners may be configured to accurately position the substrate in relation to a measurement optical system. Various sensors and actuators are provided for example to acquire the position of a target of interest, and to bring it into position under the objective lens 16. Typically many measurements will be made on targets at different locations across substrate W. The substrate support can be moved in X and/or Y directions to acquire different targets, and in the Z direction to obtain a desired focusing of the optical system on the target. It is convenient to think and describe operations as if the objective lens and optical system being brought to different locations on the substrate, when in practice the optical system may remain substantially stationary and only the substrate moves. In other apparatuses, relative movement in one direction is implemented by physical movement of the substrate, while relative movement in orthogonal direction is implemented by physical movement of the optical system. Provided the relative position of the substrate and the optical system is correct, it does not matter in principle whether one or both of those is moving in the real world.

When the radiation beam is incident on the beam splitter 16 part of it is transmitted through the beam splitter (partially reflecting surface 15) and follows a reference path RP towards a reference mirror 14.

Radiation reflected by the substrate, including radiation diffracted by any metrology target T, is collected by lens 16 and follows a collection path CP in which it passes through partially reflecting surface 15 into a detector 19. The detector may be located in the back-projected pupil plane P, which is at the focal length F of the lens 16. In practice, the pupil plane itself may be inaccessible, and may instead be re-imaged with auxiliary optics (not shown) onto the detector located in a so-called conjugate pupil plane P'. The detector may be a two-dimensional detector so that a two-dimensional angular scatter spectrum or diffraction spectrum of a substrate target 30 can be measured. In the pupil plane or conjugate pupil plane, the radial position of radiation defines the angle of incidence/departure of the radiation in the plane of focused spot S, and the angular position around an optical axis O defines azimuth angle of the radiation. The detector 19 may be, for example, an array of CCD or CMOS sensors, and may use an integration time of, for example, 40 milliseconds per frame.

Radiation in reference path RP is projected onto a different part of the same detector 19 or alternatively on to a different detector (not shown). A reference beam is often used for example to measure the intensity of the incident radiation, to allow normalization of the intensity values measured in the scatter spectrum.

The various components of illumination system 12 can be adjustable to implement different metrology 'recipes' within the same apparatus. Color filter 12b may be implemented for example by a set of interference filters to select different wavelengths of interest in the range of, say, 405-790 nm or even lower, such as 200-300 nm. An interference filter may be tunable rather than comprising a set of different filters. A grating could be used instead of interference filters. Polarizer 12c may be rotatable or swappable so as to implement different polarization states in the radiation spot S. Aperture device 13 can be adjusted to implement different illumination profiles. Aperture device 13 is located in a plane P'" conjugate with pupil plane P of objective lens 16 and the plane of the detector 19. In this way, an illumination profile defined by the aperture device defines the angular distribution of light incident on substrate radiation passing through different locations on aperture device 13.

The detector 19 may measure the intensity of scattered light at a single wavelength (or narrow wavelength range), or it may measure the intensity separately at multiple wavelengths, or integrated over a wavelength range. Furthermore, the detector may separately measure the intensity of transverse magnetic- and transverse electric-polarized light and/or the phase difference between the transverse magnetic-polarized light and transverse electric-polarized light.

In the known angle-resolved scatterometer represented schematically in FIG. 2, a metrology target T is provided on substrate W. For measurements, this target may comprise a 1-D grating, which is printed such that after development, it is an array of solid resist lines. Alternatively, the target may be a 2-D grating, which is printed such that after development, the grating is formed of solid resist pillars or vias (contact holes) in the resist. The bars, pillars or vias may alternatively be etched into the substrate. Measurements of parameters such as line widths and shapes, may be obtained by an iterative reconstruction process, performed by processing unit PU, from knowledge of the printing step and/or other scatterometry processes.

In addition to measurement of parameters by reconstruction, angle-resolved scatterometry is useful in the measurement of asymmetry of features in product and/or resist patterns. A particular application of asymmetry measurement is for the measurement of overlay, where the target comprises one set of periodic features superimposed on another. The concepts of asymmetry measurement using the instrument of FIG. 2 are described for example in published patent application US2006066855A1 cited above. Simply stated, while the positions of the higher diffraction orders ($1^{st}$ order and above) in the diffraction spectrum of a periodic target are determined only by the periodicity of the target, asymmetry of intensity levels in the diffraction spectrum is indicative of asymmetry in the individual features which make up the target. In the instrument of FIG. 2, where detector 19 may be an image sensor, such asymmetry in the higher diffraction orders appears directly as asymmetry in the pupil image recorded by detector 19. This asymmetry can be measured by digital image processing in unit PU, and calibrated against known values of overlay.

For very fine product structures having features many times smaller than the wavelength of the illuminating radiation, however, higher order diffraction signals are not captured by collection path CP of the optical system. Accordingly, conventional methods of diffraction-based overlay measurement are not able to reveal the type of overlay errors that may cause performance issues in very fine product structures formed by a modern multiple-patterning process.

Figure 3:
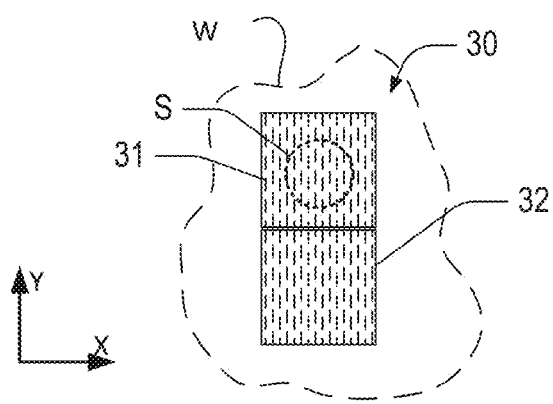
FIG. 3 illustrates a target structure according to a first embodiment of the present invention.

FIG. 3 shows a measurement target 30 formed on a substrate W according to an embodiment of the present disclosure. The measurement target comprises a first target structure 31 and a second target structure 32. Examples of these will be described in greater detail below with reference to FIG. 6. Both the first target structure and the second target structure are comprised of features which have dimensions similar to those of product features. The first target structure and second target structure may be formed in the same material layer as product features formed on the same substrate, and may be formed by the same processes as the product features. For example, the first target structure and the second target structure may be formed in a single layer by multiple patterning steps. In another example, the first target structure and the second target structure are formed by the same etching steps as product structures on the substrate. Such product structures may be formed elsewhere on the same substrate, or it may be a substrate dedicated to carrying metrology targets only. In this regard, the substrate W in this example may be one of the substrates 232 or 234 in the process illustrated in FIG. 1, rather than one of the substrates 220 that have not yet ben etched.

In the example, both the first target structure and the second target structure are two-dimensional structures, with periodicity in at least some features along one or both of the X direction or the Y direction. Whatever the periodicity of the structure as a whole, features within the structure are arrayed in a first direction (e.g. the X direction)with a pitch (spatial period) similar to that of product features to be formed by the lithographic process under investigation. Each target structure as a whole may be periodic in one or more directions.

Whatever the periodicity of the structure as a whole, it is a two-dimensional structure in the sense that it has features varying in both the X direction and the Y direction. By comparison, a "one-dimensional" grating structure may extend in two dimensions over an area of a substrate, but (at least within the illumination spot S of the metrology apparatus) varies only in one direction. In other words, references to two-dimensional structures in the present disclosure can be interpreted so that each target structure comprises features having non-zero components in a complementary Fourier space in both $k_x$ and $k_y$ directions (k are wavenumbers).

As can be seen, the measurement target 30 in this example has a set of dimensions that are bigger than the irradiation spot S of the metrology apparatus. This is also known as "underfilling" the target, and avoids interference of other structures in the obtained signals. For example, the target may be 40×40 µm or larger. With an appropriate illumination system, it is possible to reduce the size of the irradiation spot. This would enable a commensurate reduction of the size of the target, for example as small as 10×10 µm. Reducing the size of a measurement target is important as it enables the target to be placed within product areas on a substrate without using excessive amounts of substrate real estate, which can otherwise be used for product structures.

In this example, the targets structures 31, 32 are each periodic in both a first (X) direction and a second (Y) direction. The first target structure 31 and the second target structure 32 are in one embodiment defined by of a first set of features and a second set of features. In one embodiment, represented schematically in FIG. 3, the first features comprise a plurality of linear elements defined by a first lithographic step, the linear elements being arranged in a periodic arrangement. In this embodiment, the plurality of linear elements are modified by the second set of features to form a two-dimensional periodic structure. Specifically, the second set of features, comprises a periodic arrangement of locations where portions of the linear elements have been removed. The locations of these "cuts" are defined by the second lithographic process, and have a two-dimensional periodic arrangement. Typically the shortest pitch (highest spatial frequency) of all the spatial frequency components will be that of the grid formed using the first lithographic step. The grid may be one-dimensional or two-dimensional. The two-dimensional structure comprising a grid of linear elements with cuts is similar in its spatial frequency components to product structures that are to be produced on the same or another substrate using the same lithographic process.

Figure 4:
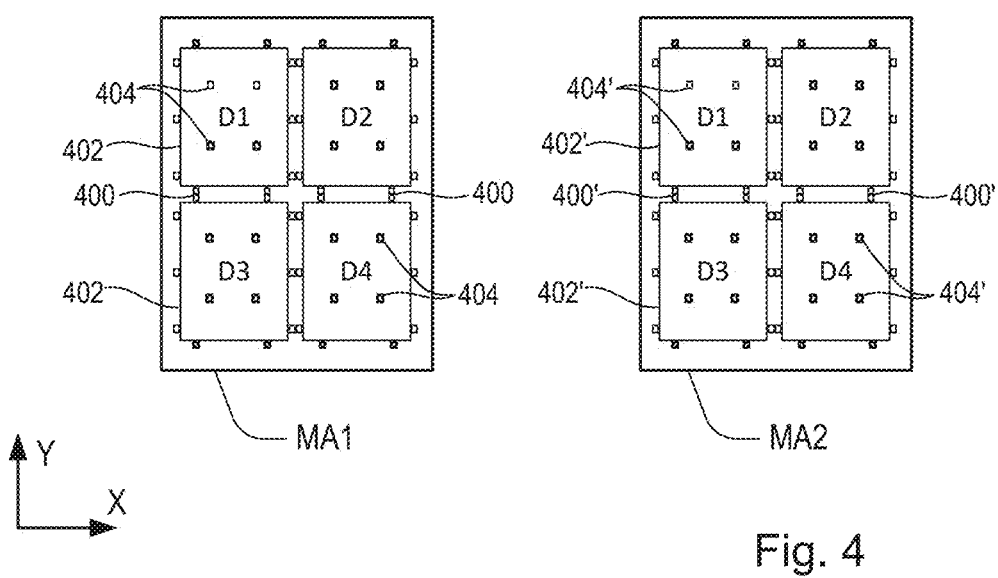
FIG. 4 schematically illustrates part of a set of patterning devices used applying patterns to a substrate in the formation of the target structures of FIG. 3.

FIG. 4 shows schematically the overall layout of a first patterning device MA1, such as a reticle. The patterning device MA1 may comprise features 400 defining a number of metrology targets and functional product pattern areas 402. As is well known, patterning device M may contain a single product pattern, or an array of product patterns if the field of the lithographic apparatus is large enough to accommodate them. The example in FIG. 4 shows four product areas labeled D1 to D4. Target features 400 are placed in scribe lane areas adjacent these device pattern areas and between them. The substrate W will eventually be diced into individual products by cutting along these scribe lanes, so that the presence of the targets does not reduce the area available for functional product structures. Where targets are small enough, they may also be deployed within the product areas 402, to allow closer monitoring of lithography and process performance across the substrate. Some in-die target features 404 of this type are shown in product areas D1-D4.

While FIG. 4 shows the patterning devices MA1 the same pattern is reproduced on the substrate W after the first lithographic step, and consequently the above description applies to the substrate W as well as the patterning device. Often a feature on the substrate will be defined directly by corresponding features on the patterning device. As is also known, however, the relationship between the pattern on the patterning device and the finished features on the substrate is more complex. This can be especially so when techniques such as pitch multiplication and multiple patterning are applied in the processes described here.

Additionally, a second patterning device MA2 is shown in FIG. 4. A separate patterning device is needed for each lithographic step of the lithographic process. These patterning devices are just two among a larger set of patterning devices that will be used in a sequence of lithographic steps to make a finished product by the process illustrated in FIG. 1. In this example, the patterning devices MA1 and MA2 are designed to be used together in a multiple patterning process, so as to define target structures and product structures within a single material layer.

Similarly to the first patterning device, the second patterning device comprises a number of metrology target features 400' and a number of functional product areas 402'. The layout is very similar between the two patterning devices at a macroscopic level, but at the microscopic level the patterns may be very different. Thus, the second patterning device may define new features of the target structures and/or functional product patterns, to be added to features defined in the first lithographic step. Alternatively, or in addition, the second patterning device may define features which modify the features defined in a first lithographic step. As an example, the first patterning device MA1 may define (directly or indirectly) a grid of features that are formed on the substrate using a first lithographic process. The second patterning device MA2 may define a number of features which modify elements of the grid structure, during a second lithographic process.

Figure 5A:
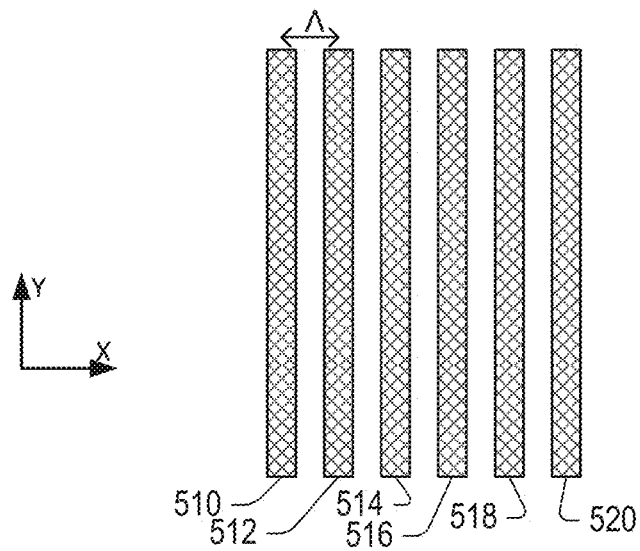
FIGS. 5(*a*)-5(*c*) schematically illustrate stages in a known multiple patterning process.
Figure 5B:
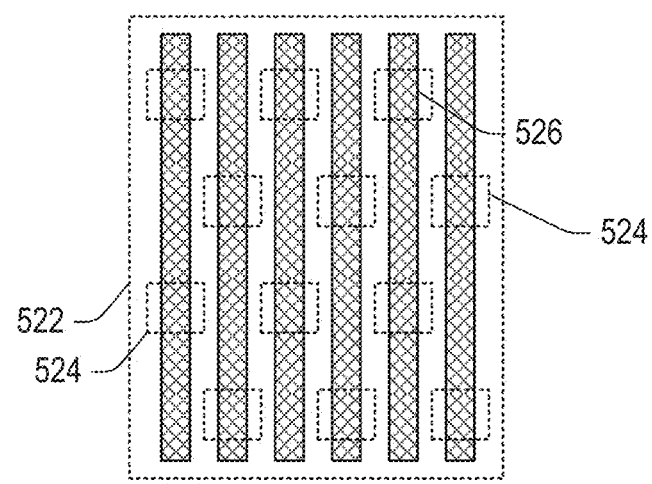
Figure 5C:
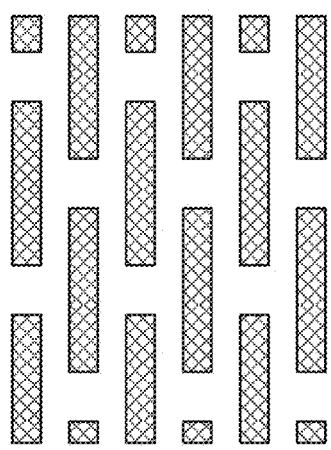

Referring now to FIG. 5, an example of multiple patterning to form a product structure on a substrate is illustrated. At (a), a first grid structure can be seen that comprises a plurality of grid elements 510, 512, 514, 516, 518, 520 that are arranged in a periodic arrangement in a first direction. The features of the first grid structure have been defined by a first patterning device MA1 in a first lithographic step. In an example, however, the grid structure is not defined directly by the patterning on the first patterning device, but has been formed by using pitch multiplication (e.g. doubling, quadrupling). Pitch multiplication allows the production of structures having a far finer pitch than anything that can be formed directly using lithographic apparatus LA. It is of course to be noted that pitch multiplication is merely one exemplary method for forming grid structures.

The next process step to form a functional device pattern by multiple patterning typically involves local modification of some or all elements of the grid structure. In the present example, modification involves removing material at selected locations along the elements of the first grid structure, so as to cut each grid element into a number of individual elements. In the finished product, the elements may for example perform metallic conductors, connecting functional devices and other conductors formed in layers above and/or below the layer shown. Other types of modification may be envisaged in principle, and cutting will be used as an illustration in the following description, only because it is the most common example of modification. Also, modification of the elements should be understood as one example of modification of the first gird structure generally. Modification of the first grid structure could for example include locally bridging a gap between elements, rather than modifying the elements themselves. In this way, the gaps between elements become divided into disconnected gaps, which may be useful in forming functional device structures in subsequent process steps.

To achieve the local cutting of the grid elements 510, 512, 514, 516, 518, 520, a second lithographic process is performed using second patterning device MA2 to define a cut mask 522, illustrated by the dashed line in view (b). Cut mask 522 can be formed of photosensitive resist material which substantially covers the first grid structure, except for small apertures 524. A patterning device (MA in FIG. 1) can be provided with the appropriate pattern to form the cut mask apertures directly by imaging in the resist, or indirectly in some way. As can be seen in view (b), small portions 526 of the grid elements are exposed in the apertures 524. In the present example, the apertures 524 are arranged in a periodic manner in both the first and a second direction orthogonal to the first direction. The periodicity of the cut mask pattern is lower (longer period; lower spatial frequency) than the grid structure with pitch Λ. Embodiments wherein the apertures are arranged in a periodic manner in only one of the first direction and the second direction may also be envisaged. By a suitable etching process, all the exposed portions of the grid elements 510, 512, 514, 516, 518, 520 are removed. After the cut mask 522 is removed, we see at (c) the functional device pattern which comprises the grid elements, separated by cuts or gaps. This device pattern may be the finished product structure, or some intermediate structure to which further steps are applied to produce the finished product based on this pattern.

For the purposes of this example, only one processing step has been shown in FIG. 5. In practice, further processes, including application of further grid elements, may be carried out to form a functional device structure in accordance with a particular pattern.

Figure 6A:
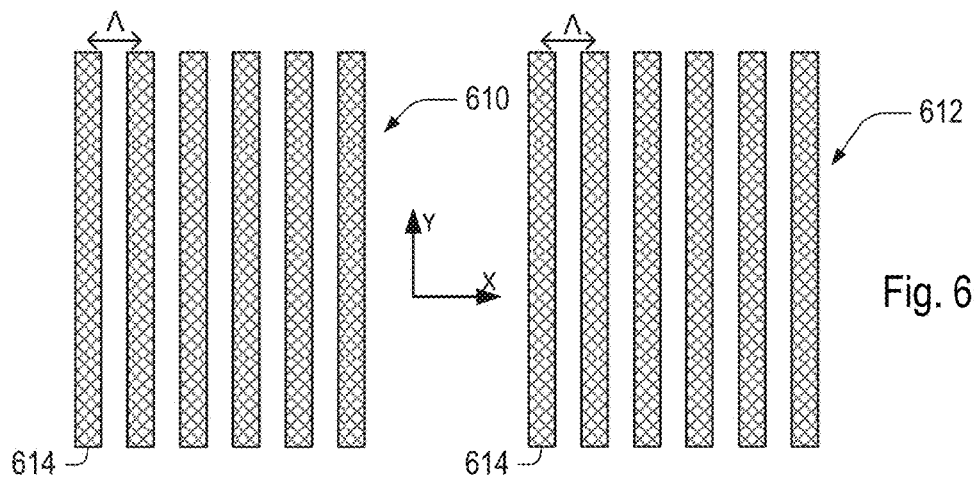
FIGS. 6(*a*)-6(*c*) illustrate stages in forming first and second target structures in a multiple patterning process according to an embodiment of the present invention.
Figure 6B:
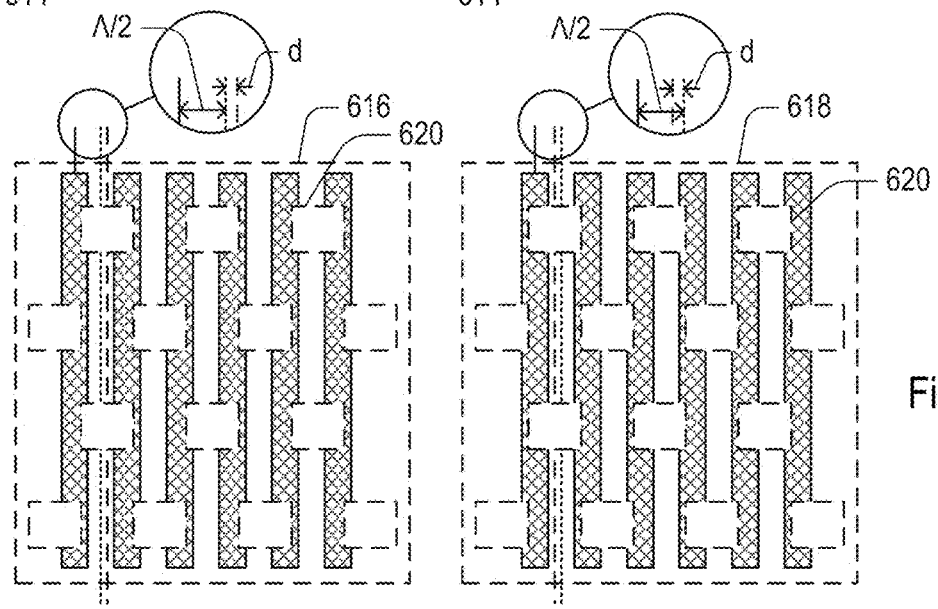
Figure 6C:
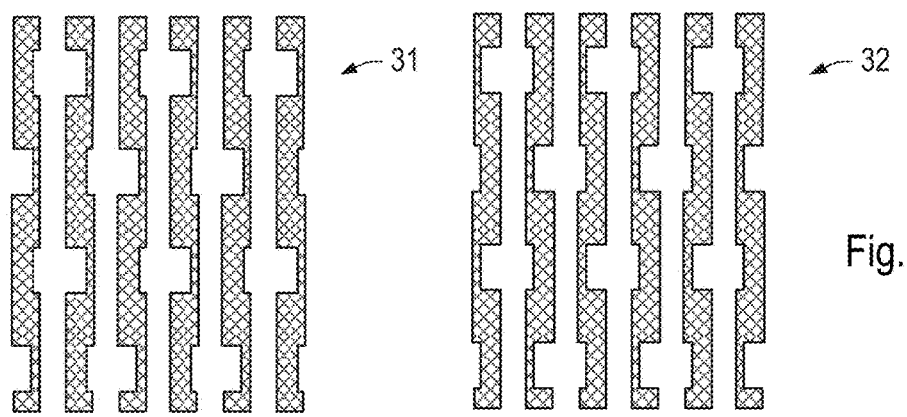

Referring to FIGS. 6, a method is shown for forming the metrology target 30 shown in FIG. 3 by the process described with reference to FIG. 5. As described above, the target structure is formed of a first target structure 31 and a second target structure 32. Each target structure comprises features defined by a first lithographic step and features defined by a second lithographic step. In the present example, formation of the first target structure begins at (a) with a first grid structure 610 and the second target structure begins with a second grid structure 612. These features comprise a grid structure that is comprised of a periodic array of grid elements 614 spaced with a pitch Λ in the first (e.g. X) direction. The grid elements are arranged in a periodic arrangement in the first direction with a pitch Λ that is similar or identical to that of corresponding product structures on the same substrate. Each grid element in this example comprises a linear element which extends in the second (Y) direction.

The grid structures 610 and 612 are shown and labelled as distinct structures purely for explanation. In a practical embodiment, a single grid structure may extend uniformly throughout both metrology target areas, and also though product areas (402) where present. (The difference between product areas and metrology target areas in such a case is made in a second lithographic step, as described below.) It is, of course, to be noted that this value is exemplary only, and that any suitable value can be chosen for the pitch Λ. Typically, the pitch should match the pitch of the product features, so that ultimately any measured parameter relates accurately to what is achieved in the real product. In one example, the pitch is Λ=40 nm. The pitch is several times smaller than the wavelength of radiation used in a typical scatterometer, which may be in the range for example 400-700 nm. The techniques described herein may be use where the pitch of an underlying periodic structure is less than a fifth, or less than a tenth of the wavelength of the radiation used in a measurement.

Subsequently, during the second lithographic step and suitable processing modifications to the grid structure are made to form the product structure (if present on the same substrate) and the first and second target structures 31, 32.

To form the first target structure 31, a first cut mask 616 is formed using the second patterning device MA2 in the second lithographic step, as shown at (b). This cut mask comprises a plurality of apertures 620, the apertures in this example being arranged in a periodic manner in both the first and second directions. In the present example, the apertures are illustrated as rectangular, although it is, of course, to be appreciated that the apertures could be any suitable shape, and may be distorted when produced in the real process. The apertures 620 of the first cut mask 616 are arranged on the cut mask so as to be offset from the grid elements by a known amount (also known as "bias"). In the present example, the apertures of the first cut mask are biased by Λ/2+d, (d<<Λ), that is to say an amount close to half the pitch of the grid structure. The apertures 620 are therefore positioned so that each aperture results in a partial cut being made to one or both of the adjacent grid elements 614, rather than neatly cutting one grid element as they do in the product structure of FIG. 5. In the example with Λ=40 nm, for example, one might choose d=5 nm. It should be noted that the specific value for d is exemplary only, and that any suitable value for d could be chosen.

By setting the bias close to Λ/2 asymmetry in the target structure 31 is made more pronounced, and more sensitive to any further misplacement of the cut mask apertures, such as would be caused by overlay error. This in turn increases the asymmetry of radiation scattered by the first target structure and the sensitivity of that asymmetry to misplacement caused by overlay error.

Similarly, to form the second target structure 32, the second patterning device MA2 and the second lithographic step are used to form a second cut mask 618. The second cut mask comprises a plurality of apertures 620 in a similar arrangement to that of the first cut mask. The apertures 620 of the second cut mask 618 are biased by a different amount, still close to a half pitch when compared to their position in product areas (FIG. 5). In an example, the second target structure is formed with bias amount of Λ/2−d. The values for the pitch Λ and d are identical to those of the first cut mask, so that the bias amounts in the two target structures are spaced equally either side of a half pitch.

After completion of the etching and other process steps, the portions of the grid elements 614 that were exposed by the apertures have been removed, which results in the structures shown at (c). As can be seen, the second target structure in this example is a mirror image of the first target structure. This is only in the case where the bias amounts are spaced equally either side of the half pitch Λ/2, and in the case where overlay error between the first and second lithographic steps is zero. In a real target, with non-zero overlay error, the first and second target structures will not be mirror images of one another, and will exhibit different degrees of asymmetry within themselves. Note that, while the target structures 31, 32 are very different the product structure and more sensitive to the parameter of interest (such as overlay), they are formed by the identical steps and processing, and by identical patterns in the patterning devices MA1, MA2 as the product structures. Only the bias in their position relative to the underlying grid elements 614 is changed. In this way, the performance of the lithographic apparatus and other process steps when forming the metrology target structures should be the same as that when forming the product structures.

Referring now to FIG. 7, a method of measuring a parameter of a lithographic process 700 according to an embodiment of the present disclosure will now be described. In step 701, a first target structure and a second target structure is provided on a substrate. In the present embodiment, both target structures are formed by a process as described above with reference to FIG. 6. Of course they may be formed by whatever lithographic process is under investigation.

In step 702, a first angle-resolved scatter spectrum radiation is obtained. In the present embodiment, an angle-resolved scatterometer is used, as described with reference to FIG. 2 above. The first target structure is illuminated with a light source of selected polarization and wavelength. The zeroth order light scattered by the first target structure is collected by the optical system of the scatterometer. As explained above, the detector is located in the back-projected pupil plane P (or alternatively in the conjugate pupil plane P'). The detector 19 then captures a first scatter spectrum representing the angular distribution of zeroth order light scattered by the first target structure. In the present example, 2-D scatter spectra are obtained. In principle, only a 1-D scatter spectrum could be captured by the detector, but the 2-D scatter spectrum contains more information in practice, particularly as we are concerned in the present disclosure with two-dimensional structures formed by multiple patterning.

In step 703, a second angle-resolved scatter spectrum is collected by the detector in a similar fashion. The second target structure is illuminated with a light source. The zeroth order light scattered by the second target structure is collected by the optical system of the scatterometer. The detector then captures a second scatter spectrum representing the angular distribution of zeroth order light scattered by the second target structure.

As a preliminary step to steps 702 and 704, a process of selecting illumination conditions suitable for the specific target structures may be performed.

In step 704, a measurement of a parameter of interest is derived from an asymmetry of the first and from an asymmetry of the second angle-resolved scatter spectrum. In the present example, the parameter to be derived is overlay error, which is determined as described in the following. In other examples, the parameter of interest may be exposure dose, focus or asymmetric lens aberration.

To measure asymmetry of the scatter spectrum, in one example a processing unit generates a first differential scatter spectrum by subtracting from the first scatter spectrum a 180-degree rotated copy of itself. The processing unit then generates a second differential scatter spectrum by subtracting from the second scatter spectrum an inverted copy of itself. Asymmetries $A_{\Lambda/2+d}$ for the first target structure, and $A_{\Lambda/2-d}$ for the second target structure, are then determined based on the first and second differential scatter spectrums. In a simple example, the average pupil asymmetry is calculated simply by subtracting the mean of all the pixel values in the left half of the differential scatter spectrum from the mean of all the pixel values in the right half. Alternative or more sophisticated asymmetry measures can be envisaged, for example in order to maximize use of the available signal. Optionally, the average pupil asymmetry can be normalized to the overall average intensity, as normalized asymmetry measurements are more comparable with one another.

Figure 8:
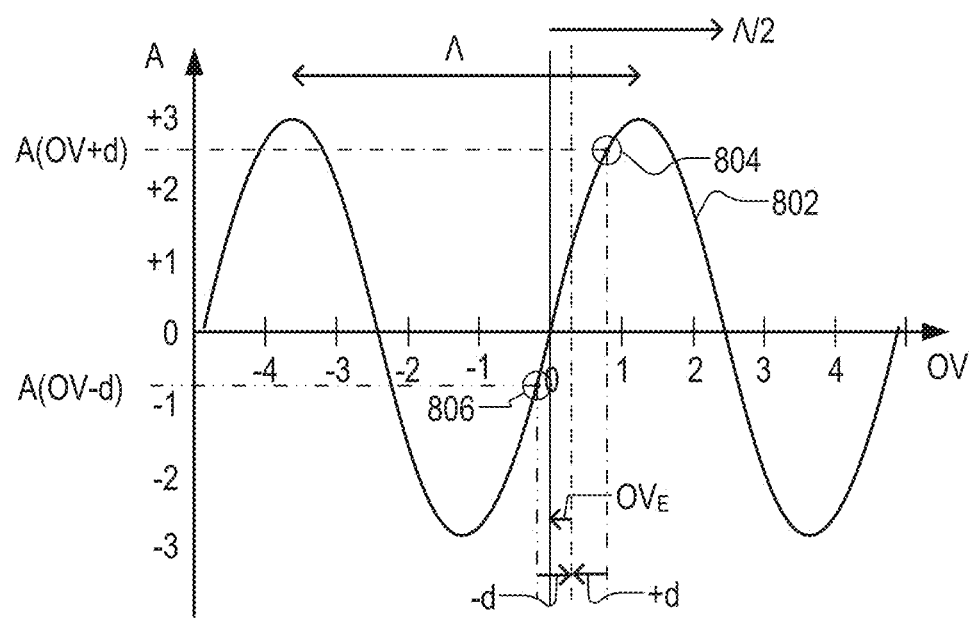
FIG. 8 schematically illustrates the principles of a conventional method of measuring overlay.

In FIG. 8 a curve 802 illustrates the relationship between overlay OV and asymmetry A in a conventional diffraction-based overlay measurement. The conventional overlay measurement will be described here purely as background. The curve normal represents asymmetry between $+1^{st}$ and $-1^{st}$ order diffraction signals. The idealized curve also assumes an 'ideal', one-dimensional target structure having no offset and no structural asymmetry within the individual structures forming the target structure. Consequently, the asymmetry of this ideal target structure comprises only an overlay contribution due to misalignment of the first features and second features. This overlay contribution results from a combination of a known imposed bias amount and an (unknown) overlay error. This graph is to illustrate the principles behind the disclosure only, and the units of asymmetry A and overlay OV are arbitrary. Examples of actual dimensions will be given further below.

In the 'idealized' situation of FIG. 8, the curve 802 indicates that the intensity asymmetry A has a non-linear periodic relationship (for example a sinusoidal relationship) with the overlay. The period Λ of the sinusoidal variation corresponds to the period or pitch Λ of the grid elements of the target structure, converted of course to an appropriate scale. The sinusoidal form is pure in this idealized example, but can include harmonics in real circumstances.

It is well known to the skilled person to use biased structures, such as gratings (having a known imposed overlay bias), to measure overlay, rather than relying on a single measurement. This bias has a known value defined in the patterning device (e.g. a reticle) from which it was made, that serves as an on-wafer calibration of the overlay corresponding to the measured intensity asymmetry. In the drawing, the calculation is illustrated graphically. As an example only, asymmetry measurements $A_{+d}$ and $A_{-d}$ are obtained for targets having imposed biases +d an −d respectively. Fitting these measurements to the sinusoidal curve gives points 804 and 806 as shown. Knowing the biases, the true overlay error $OV_E$ can be calculated. The pitch Λ of the sinusoidal curve is known from the design of the target structure. The vertical scale of the curve 802 is not known to start with, but is an unknown factor which can be referred to as a $1^{st}$ harmonic proportionality constant, $K_1$. This constant $K_1$ is a measure of the sensitivity of the intensity asymmetry measurements to the target structure.

In mathematical terms, the relationship between overlay error $OV_E$ and intensity asymmetry A is assumed to be:

$$A_{\pm d} = K_1 \sin(OV_E \pm d) \tag{1}$$

where overlay error $OV_E$ is expressed on a scale such that the target pitch Λ corresponds to an angle 2π radians. $A_{+d}$ and $A_{-d}$ represent asymmetry of the target structures with biases +d and −d respectively. Using two measurements of targets with different, known biases (e.g. +d and −d) the overlay error $OV_E$ can be calculated without knowing $K_1$ using the relationship:

$$OV_E = \operatorname{atan}\left(\frac{A_{+d} + A_{-d}}{A_{+d} - A_{-d}} \cdot \tan(d)\right) \tag{2}$$

In the present disclosure, it is proposed to use bias amounts close to a half pitch, for example bias amounts Λ/2+d and Λ/2−d. The same principles apply as in equations (1) and (2), except that the slope of the sinusoidal function will be opposite. On the other hand, in the present disclosure it is also proposed to use only zeroth order scatter spectra. The structures under investigation are periodic with periods much shorter than the wavelength λ of the illuminating radiation. The period Λ may be for example less than 0.2 λ or less than 0.1 λ, and to collect higher order diffracted radiation may be impossible with the available optical system. Strong asymmetry signals with the sinusoidal form shown in FIG. 8 are therefore not expected. The inventors have recognized that, using bias amounts close to Λ/2 instead of bias amounts close to zero can give useful asymmetry signals even in the zeroth order scatter spectrum, for 2-D product structures formed by multiple patterning in a single material layer.

Note that the pitch Λ in this context is not necessarily a periodicity of the finished 2-D target structure, but rather by the pitch of the grid formed in the first lithographic step. This will be the shortest period of several periodic components present in the overall 2-D periodic structure after the second lithographic step. While it is sensible for various reasons to use two bias values either side of Λ/2, and to have them equally spaced either side of Λ/2, this is not an essential requirement. One of the bias amounts could be exactly Λ/2, if desired; both could even be on the same side of Λ/2. The calculations can be adapted to any pair of bias values close to Λ/2. Considering what is "close to" a half pitch, this is a matter of choice and experimentation for each target. In a practical implementation, it may be desired to operate in a relatively narrow region of the sinusoidal function in Equation (1), so that the variation of asymmetry with overlay can be considered to be linear. Not only the bias amounts should be considered when identifying the operating region, but also the anticipated range of overlay error that will be added to the programmed bias in a real target structure. The bias amounts Λ/2±d for example may lie between 0.3 Λ and 0.7 Λ, or between 0.4 Λ and 0.6 Λ. In a particular example, the parameter d is chosen to be d<Λ/4. In general, the exact size of d may be optimized dependent on situational requirements and circumstances. Larger values of d may be used to improve the signal-to-noise ratio, and smaller values of d may be used to increase the accuracy of the overlay calculation.

In practice, intensity asymmetry measurements are not only dependent on the properties of the target structures, but are also dependent on the properties of the light incident on the target structures.

Figure 9:
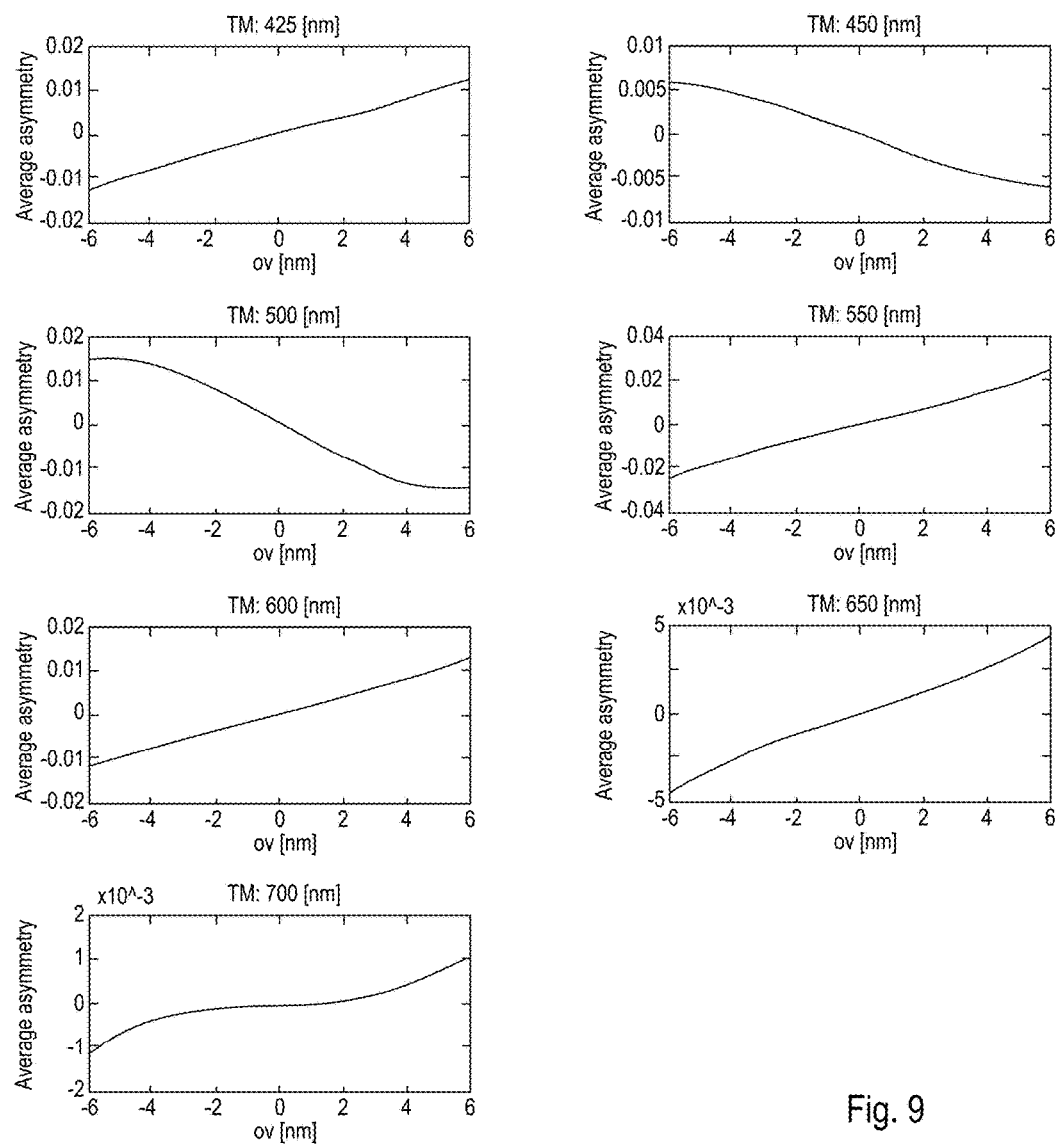
FIG. 9 illustrates simulated variation of asymmetry against overlay, for different wavelengths of radiation scattered from the example target structure.

FIG. 9 shows a number of exemplary simulated results for an exemplary target structure, each simulation having been performed using light with a particular wavelength. Each graph shows the normalized average asymmetry for a measurement target with target structures as described with reference to FIG. 6. Overlay is plotted over the horizontal axis, while an amplitude of the asymmetry signal is plotted on the vertical axis. In each case, the average pupil asymmetry has been normalized to the overall average intensity. The wavelength of radiation used in each measurement is shown by a label, ranging from 425 nm at top left, through to 700 nm at bottom. In the example simulated here, the first features of the first target structure and the third features of the second target structure both have a pitch Λ=40 nm. The third features of the first target structure may be biased for example by Λ/2+d, where d=5 nm. The fourth features of the second target structure are biased by Λ/2−d.

In the present example, the asymmetry varies dependent on the wavelength used in the measurement. By selecting the wavelength of the light used, it is possible to maximize the accuracy of the measurement. Different wavelengths and polarizations may be more successful for a different processes and different target designs. In the illustration of FIG. 9, TM polarization is chosen for all graphs, but polarization is a parameter of illumination that can be varied if desired.

Measurements can be taken at more than one wavelength and/or polarization, if desired, for further improving accuracy of the measurement. Results from different wavelengths can be combined in any suitable manner, either before or after conversion to overlay values. Note that it may be desirable to optimize not only the amplitude of the asymmetry signal (vertical scale in FIG. 9 graphs), but also the linearity of the curve. The wavelength(s) selected should be one (or more than one) for which a strong signal is obtained which is more or less linear over the range of values expected for overlay (or other parameter of interest). Among the examples illustrated in FIG. 9, simple inspection can be used to select the best one for a given target structure.

Figure 10:
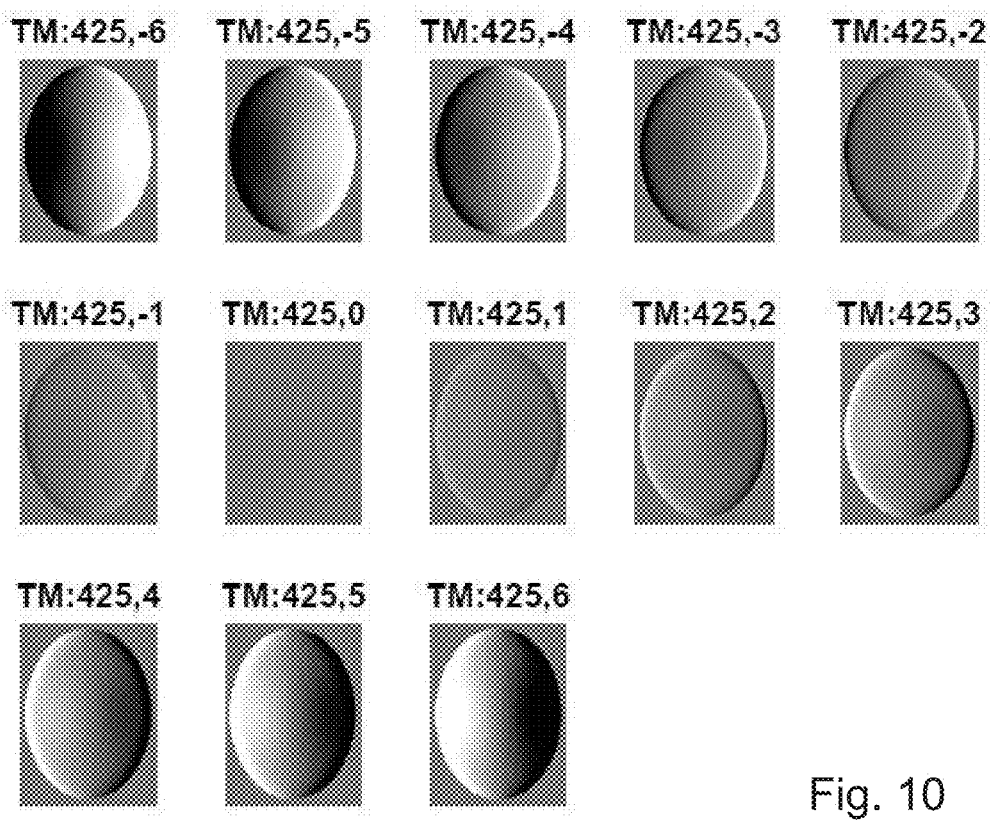
FIG. 10 shows simulated pupil images of asymmetry in scatter spectra of an example target structure with different overlay values.

FIG. 10 shows a number of exemplary simulated pupil images for one of the radiation wavelengths shown in FIG. 9. Each image shows the simulated pupil image for a given value of overlay. The radiation wavelength and the overlay amount is shown by a label above each image. As can be seen, the wavelength of the radiation used is 425 nm and the overlay values range from −6 nm to +6 nm.

The dimensions of the modern product structures are so small that they cannot be imaged by optical metrology techniques. Small features include, for example, those formed by multiple patterning processes, and pitch-multiplication (terms explained further above). In effect, the structures are too small for traditional metrology techniques which cannot "see" them. Hence, targets used for high-volume metrology often use features that are much larger than the products whose overlay errors or critical dimensions are the property of interest.

While scanning electron microscopes are able to resolve modern products structures, measurements performed with scanning electron microscopes are much more time consuming, as well as more expensive, than optical measurements and result in the destruction of the measured wafer.

The inventors have recognized that it is possible to perform metrology measurements on structures with dimensions and processing similar to product structures, or on structures formed from product structures, by using zeroth order light scattered by these structures. Furthermore, it was recognized that using asymmetrical contribution of the measured spectrum, weighted by a careful choice of weighting coefficients, it is possible to determine an overlay error between two steps of multi-patterning process, for example.

In an aspect, there is provided a method of measuring a parameter of a lithographic process comprising; illuminating a target structure with radiation wherein the target structure is formed by said lithographic process, obtaining an angle-resolved scatter spectrum of the target structure; and deriving a measurement of said parameter using asymmetry found in the scatter spectrum of the target structure.

In some embodiments, using the asymmetry found in the scatter spectrum of the target structure comprises using regions of the scatter spectrum which are being equally spaced from a reference.

In some embodiments, the contribution of the asymmetry, found in the scatter spectrum of the target structure used in deriving of the parameter of the lithographic process, is modified by a weighting coefficient.

Further, the illumination of the metrology apparatus described in FIG. 2, can be directed towards regions of the wafer W containing a pattern forming product structures. In usual experimental conditions, when forming a product as a result of exposure of at least two patterning devices, it is expected that an overlay error will appear, overlay error being between said formed pattern structures. As a way of an example, the two patterns can be formed by a patterning device corresponding to a periodic line structure and a patterning device corresponding to a cut mask.

The target structure, formed by product structures as described in the paragraph above, or formed by structures similar to product structures, is illuminated with a light source of selected polarization and wavelength. The zeroth order light scattered by the target structure is collected by the optical system of the scatterometer. As explained above, the detector is located in the back-projected pupil plane P (or alternatively in the conjugate pupil plane P'). The detector 19 then captures a first scatter spectrum representing the angular distribution of zeroth order light scattered by the first target structure. In the present example, 2-D scatter spectra are obtained. In principle, only a 1-D scatter spectrum could be captured by the detector, but the 2-D scatter spectrum contains more information in practice, particularly as we are concerned in the present disclosure with two-dimensional structures formed by multiple patterning. Therefore, a parameter of a lithographic process is measured with a method comprising: illuminating a target structure with radiation wherein the target structure is formed by said lithographic process, obtaining an angle-resolved scatter spectrum of the target structure; and deriving a measurement of said parameter using asymmetry found in the scatter spectrum of the target structure.

Further, the method is using regions of the scatter spectrum which are being equally spaced from a reference when using the asymmetry found in the scatter spectrum of the target structure. For example, when the measured spectrum is a 2-D scatter spectrum, measured in the pupil plane P, the reference can be one of the two axes of 2-D coordinate system. In this case, the reference can be the x-axis or the y-axis. It should be recognized that the x-axis and the y-axis form symmetry references as a line. Further, in the same 2-D coordinate system, the origin of the coordinate system can be considered a reference as well. In this case, the reference would be a point.

The step of deriving a measurement of a parameter of a lithographic process uses regions of the 2-D measured spectrum, as found in the pupil P, regions which are symmetrical with respect to a reference. By subtracting said symmetrical contribution of the pupil, one is able to find an indication of a degree of asymmetry present in the measured 2-D spectrum. The step of subtracting said symmetrical portions of the pupil forms a characteristic SS. The asymmetry of the 2-D spectrum is correlated to the overlay error between patterned structures formed in different lithographic steps, for example. The regions which are used in deriving the overlay error can be single pixels or can be groups of pixels, said groups having an internal symmetry, or said groups having no symmetry at all.

Further, the contribution of the asymmetry, found in the scatter spectrum of the target structure used in deriving of the parameter of the lithographic process, is modified by weighting coefficients. Each characteristic SS will represent an indication of the asymmetry of the 2-D spectrum as measured in the pupil and an indication of the symmetry of the asymmetry as present in the 2-D scatter spectrum. It is recognized that one can measure multiple SS characteristics, each one of the SS characteristics being a contribution from a different region of the measured 2-D spectrum or obtained by using different weighting coefficients. By introducing a weighting factor for each characteristic SS, it is possible to enhance detection of the overlay error.

In an embodiment, the weighting coefficient is obtained from the asymmetric Jacobian part of the symmetric position. The region in the 2-D spectrum sensitive to the overlay error can be obtained by computing the Jacobian for the nominal target model of the target structure using an analytical or computational method, such as, for example, RCWA. The weighting coefficients follow from the asymmetric part of this Jacobian.

In an embodiment, the weighting coefficient is obtained from the asymmetric Jacobian calculated at different overlay errors. Due to non-linear 2-D spectrum responses, the Jacobian may change when the target structure changes due to process variations. The asymmetric part of a (weighted) Jacobian average, obtained from models of the target structure corresponding to different process variations, can be used to make the overlay measurement more robust to process variations.

In an embodiment, the weighting coefficient is obtained from a Design of Experiment (DoE). A DoE can be used to determine the region in the measured 2-D spectra that is sensitive to the overlay error, by, e.g., applying a PCA (principal component analysis) to the asymmetry of these measured 2-D spectra. The weighting scheme directly follows from one or more obtained principal components.

Although patterning devices in the form of a physical reticle have been described, the term "patterning device" in this application also includes a data product conveying a pattern in digital form, for example to be used in conjunction with a programmable patterning device.

Further embodiments according to the invention are provided in below numbered clauses:

1. A method of measuring a parameter of a lithographic process, the lithographic process being for forming a two-dimensional, periodic product structure in a single material layer using two or more lithographic steps, the method comprising:

providing first and second target structures, each target structure comprising a two-dimensional periodic structure formed in a single material layer on a substrate using first and second lithographic steps, wherein, in the first target structure, features defined in the second lithographic step are displaced relative to features defined in the first lithographic step by a first bias amount that is close to one half of a spatial period of the features formed in the first lithographic step, and, in the second target structure, features defined in the second lithographic step are displaced relative to features defined in the first lithographic step by a second bias amount close to one half of said spatial period and different to the first bias amount;

obtaining an angle-resolved scatter spectrum of the first target structure and an angle-resolved scatter spectrum of the second target structure; and deriving a measurement of said parameter using asymmetry found in the scatter spectrum of the first target structure and asymmetry found in the scatter spectrum of the second target structure.

2. A method according to clause 1, wherein obtaining the angle-resolved scatter spectrum of each target structure comprises:

illuminating the target structure with radiation; and detecting the angle-resolved scatter spectrum using zero order radiation scattered by the target structure.

3. A method according to clause 1 or 2, wherein the spatial period of each target structure is significantly shorter than a wavelength of the radiation used to illuminate the target structures.

4. A method according to clause 2 or 3, further comprising selecting the wavelength of radiation from a range of available wavelengths so as to optimize strength and linearity of asymmetry in the angle-resolved scatter spectra of the target structures.

5. A method according to any preceding clause, wherein the step of deriving said parameter comprises calculating a measurement of overlay error relating to said product structures using the asymmetry found in the scatter spectrum of the first target structure, the asymmetry found in the scatter spectrum of the second target structure and knowledge of the first bias amount and the second bias amount.

6. A method according to any preceding clause wherein features of said target structures that are defined in the first lithographic step comprise a grid structure defining said spatial period in a first direction, and features of said target structures that are defined in the second lithographic step comprise modifications of the grid structure at locations spaced periodically in a two-dimensional periodic arrangement.

7. A method according to any preceding clause wherein the features of said target structures that are defined in the first lithographic step comprise a grid structure defining said spatial period in a first direction, and features of said target structures that are defined in the second lithographic step comprise cuts in elements of the grid structure.

8. A method according to any preceding clause, wherein the first target structure and the second target structure have been formed by etching and/or deposition processes after the first and second lithographic steps have been used to define their features.

9. A method according to any preceding clause, wherein a product structure has been formed in the same material layer elsewhere on the same substrate using said first and second lithographic steps, and wherein, in the product structure, features defined in the second lithographic step are not displaced relative to features defined in the first lithographic step by any bias amount.

10. A substrate for use in measuring a parameter of a lithographic process, the substrate comprising first and second target structures, each target structure comprising a two-dimensional periodic structure formed in a single material layer using said first and second lithographic steps, wherein, in the first target structure, features defined in the second lithographic step are displaced relative to features defined in the first lithographic step by a first bias amount that is close to one half of a spatial period of the features formed in the first lithographic step, and, in the second target structure, features defined in the second lithographic step are displaced relative to features defined in the first lithographic step by a second bias amount that is close to one half of said spatial period and different to the first bias amount.

11. A substrate according to any preceding clause wherein features of said target structures that are defined in the first lithographic step comprise a grid structure defining said spatial period in a first direction, and features of said target structures that are defined in the second lithographic step comprise modifications of the grid structure at locations spaced periodically in a two-dimensional periodic arrangement.

12. A substrate according to any preceding clause wherein the features of said target structures that are defined in the first lithographic step comprise a grid structure defining said spatial period in a first direction, and features of said target structures that are defined in the second lithographic step comprise cuts in elements of the grid structure.

13. A substrate according to any preceding clause, wherein the first target structure and the second target structure have been formed by etching and/or deposition processes after the first and second lithographic steps have been used to define their features.

14. A substrate according to any of clauses 10 to 13, wherein a product structure has been formed in the same material layer elsewhere on the same substrate using said first and second lithographic steps, and wherein, in the product structure, features defined in the second lithographic step are not displaced relative to features defined in the first lithographic step by any bias amount.

15. A set of patterning devices adapted for defining features of the first and second target structures in a lithographic process for the manufacture of a substrate according to any of clauses 10 to 14, the set of patterning devices including a first patterning device for use in said first lithographic step and a second patterning device for use in said second lithographic step to form said first and second target structures in said material layer.

16. A set of patterning devices according to clause 15, wherein said patterning devices are further adapted for defining features of a product structure in the same material layer elsewhere on the same substrate using said first and second lithographic steps, and wherein, in the product structure, features defined in the second lithographic step are not displaced relative to features defined in the first lithographic step by any bias amount.

17. A metrology apparatus arranged to perform the method of any of clauses 1 to 9.

18. A metrology apparatus according to clause 17, further comprising: a support for a substrate on which a first target structure and a second target structure have been formed;

an optical system for selectively illuminating each target structure with radiation and collecting at least zero order radiation scattered by the target structure;

a detector for detecting an angle-resolved scatter spectrum of each using said zero order radiation; and a processor arranged to derive a parameter of a lithographic process using asymmetry of the angle-resolved scatter spectrum of the first target structure and asymmetry of the angle-resolved scatter spectrum of the second target structure.

19. A lithographic system comprising:

a lithographic apparatus for use in a lithographic process; and a metrology apparatus according to clause 17 or 18 for use in measuring a parameter of the lithographic process using first and second target structures formed at least partially using the lithographic apparatus.

20. A computer program product comprising machine readable instructions which, when run on a suitable processor, cause the processor to perform the deriving step of the method of any of clauses 1 to 9.

21. A computer program product according to clause 20, further comprising machine readable instructions for controlling a metrology apparatus to illuminate said first and second target structures with radiation and to detect said angle-resolved scatter spectra for use in the deriving step.

22. A method to determine an overlay error on a substrate on which product structures have been formed, the product structures including first product features that have been defined by a first lithographic process and second product features that have been defined by a second lithographic process, the overlay error comprising a positional deviation between the first product features and the second product features, the method comprising:

providing a first target structure on the substrate, the first target structure comprising first target features defined by the first lithographic process and second target features defined by the second lithographic step, a positional relationship between the first target features and the second target features depending on a first bias value and the overlay error; and providing a second target structure on the substrate, the second target structure comprising third target features defined by the first lithographic process and fourth target features defined by the second lithographic step, a positional relationship between the third target features and the fourth target features depending on a second bias value and the overlay error;

detecting a first angle-resolved scatter spectrum using zero order radiation diffracted from the first target structure;

detecting a second angle-resolved scatter spectrum using zero order radiation diffracted from the second target structure;

calculating a measurement of the overlay error based on asymmetry observed in the first angle-resolved scatter spectrum and the second angle-resolved scatter spectrum and on knowledge of the first bias value and the second bias value.

23. A method of measuring a parameter of a lithographic process comprising: illuminating a target structure with radiation wherein the target structure is formed by said lithographic process, obtaining an angle-resolved scatter spectrum of the target structure; and deriving a measurement of said parameter using asymmetry found in the scatter spectrum of the target structure.

24. A method according to clause 23, wherein obtaining the angle-resolved scatter spectrum of the target structure comprises detecting zero order radiation scattered by the target structure.

25. A method according to the clause 23, wherein each target structure comprising features forming a two-dimensional array.

26. A method according to the clause 23, wherein the target structure comprises features having non-zero components in a complementary two dimensional Fourier space.

27. A method according to any preceding clause, wherein the step of deriving said parameter comprises calculating a measurement of overlay error relating to said product structures using the asymmetry found in the scatter spectrum of the target structure.

28. A method according to the clause 24, wherein using the asymmetry found in the scatter spectrum of the target structure comprises using regions of the scatter spectrum which are being equally spaced from a reference.

29. A method according to the clause 28, wherein the reference is a line.

30. A method according to the clause 28, wherein the reference is a point.

31. A method according to the clause 28, wherein the contribution of the asymmetry, used in deriving of the parameter of the lithographic process, is modified by weighting coefficients.

32. A method according to the clause 31, wherein the weighting coefficients are obtained from the asymmetric Jacobian part of the symmetric position.

33. A method according to the clause 31, wherein the weighting coefficient is obtained from the asymmetric Jacobian calculated at different overlay errors.

34. A method according to the clause 31, wherein the weighting coefficient is obtained from a Design of Experiment.

35. A metrology apparatus arranged to perform the method of any of clauses 23 to 34.

36. A metrology apparatus according to clause 35, further comprising:

a support for a substrate on which the target structure has been formed;

an optical system for selectively illuminating each target structure with radiation and collecting at least zero order radiation scattered by the target structure;

a detector for detecting an angle-resolved scatter spectrum of each using said zero order radiation; and a processor arranged to derive a parameter of a lithographic process using asymmetry of the angle-resolved scatter spectrum of the target structure.

37. A lithographic system comprising:

a lithographic apparatus for use in a lithographic process; and a metrology apparatus according to clause 35 or 36 for use in measuring a parameter of the lithographic process using target structures formed at least partially using the lithographic apparatus.

38. A computer program product comprising machine readable instructions which, when run on a suitable processor, cause the processor to perform the deriving step of the method of any of clauses 23 to 34.

39. A computer program product according to clause 38, further comprising machine readable instructions for controlling a metrology apparatus to illuminate said first and second target structures with radiation and to detect said angle-resolved scatter spectra for use in the deriving step.

Although specific reference may have been made above to the use of embodiments of the invention in the context of optical lithography, it will be appreciated that the invention may be used in other applications, for example imprint lithography, and where the context allows, is not limited to optical lithography. In imprint lithography, a topography in a patterning device defines the pattern created on a substrate. The topography of the patterning device may be pressed into a layer of resist supplied to the substrate whereupon the resist is cured by applying electromagnetic radiation, heat, pressure or a combination thereof. The patterning device is moved out of the resist leaving a pattern in it after the resist is cured.

The terms "radiation" and "beam" used in relation to the lithographic apparatus encompass all types of electromagnetic radiation, including ultraviolet (UV) radiation (e.g., having a wavelength of or about 365, 355, 248, 193, 157 or 126 nm) and extreme ultra-violet (EUV) radiation (e.g., having a wavelength in the range of 5-20 nm), as well as particle beams, such as ion beams or electron beams.

The term "lens", where the context allows, may refer to any one or combination of various types of optical components, including refractive, reflective, magnetic, electromagnetic and electrostatic optical components.

The foregoing description of the specific embodiments will so fully reveal the general nature of the invention that others can, by applying knowledge within the skill of the art, readily modify and/or adapt for various applications such specific embodiments, without undue experimentation, without departing from the general concept of the present invention. Therefore, such adaptations and modifications are intended to be within the meaning and range of equivalents of the disclosed embodiments, based on the teaching and guidance presented herein. It is to be understood that the phraseology or terminology herein is for the purpose of description by example, and not of limitation, such that the terminology or phraseology of the present specification is to be interpreted by the skilled artisan in light of the teachings and guidance.

The breadth and scope of the present invention should not be limited by any of the above-described exemplary embodiments, but should be defined only in accordance with the following claims and their equivalents.

The invention claimed is:

1. A method of forming a target structure and measuring a parameter of a lithographic process comprising:
    forming a target structure comprising first and second targets by the lithographic process, wherein each of the first and second targets comprise a two-dimensional periodic structure formed in a single material layer on a substrate, and wherein the lithographic process comprises:
        defining features of grid elements in the first and second targets;
        modifying the features defined in the first target by removing portions of each grid element in the first target at predefined locations in the first target, each removed portion being offset from a grid element by a first bias amount that is close to one half of a spatial period of the features; and
        modifying the features defined in the second target by removing portions of each grid element in the second target at predefined locations in the second target, each removed portion from the second target being offset from a grid element by a second bias amount that is close to one half of the spatial period and different from the first bias amount;
    illuminating, using an optical system, the target structure with radiation;
    obtaining, using a detector, an angle-resolved scatter spectrum of the target structure; and
    deriving, using a processing device, a measurement of the parameter using asymmetry found in the angle-resolved scatter spectrum of the target structure.

2. The method according to claim 1, wherein the obtaining the angle-resolved scatter spectrum of the target structure comprises detecting zero order radiation scattered by the target structure.

3. The method according to claim 1, wherein the target structure comprises features forming a two-dimensional array.

4. The method according to claim 1, wherein the target structure comprises features having non-zero components in a complementary two-dimensional Fourier space.

5. The method according to claim 1, wherein the deriving the measurement of the parameter comprises calculating a measurement of overlay error relating to the first and second targets using the asymmetry found in the angle-resolved scatter spectrum of the target structure.

6. The method according to claim 1, wherein using the asymmetry found in the angle-resolved scatter spectrum of the target structure comprises using regions of the angle-resolved scatter spectrum which are being equally spaced from a reference.

7. The method according to claim 6, wherein the reference is a line.

8. The method according to claim 6, wherein the reference is a point.

9. The method according to claim 6, further comprising:
    modifying a contribution of the asymmetry, used in deriving of the measurement of the parameter of the lithographic process, by weighting coefficients.

10. The method according to claim 9, wherein the weighting coefficients are obtained from an asymmetric Jacobian part of a symmetric position.

11. The method according to claim 9, wherein the weighting coefficients are obtained from an asymmetric Jacobian calculated at different overlay errors.

12. The method according to claim 9, wherein the weighting coefficients are obtained from a Design of Experiment.

13. A metrology apparatus comprising:
    a support configured to support a substrate on which a target structure comprising first and second targets has been formed, each of the first and second targets comprising a two-dimensional periodic structure formed in a single material layer on the substrate using a lithographic process,
    wherein the lithographic process comprises defining features of grid elements in the first and second targets, modifying the features defined in the first target by removing portions of each grid element in the first target at predefined locations in the first target, each removed portion being offset from a grid element by a first bias amount that is close to one half of a spatial period of the features, and modifying the features defined in the second target by removing portions of each grid element in the second target at predefined locations in the second target, each removed portion from the second target being offset from a grid element by a second bias amount that is close to one half of the spatial period and different from the first bias amount;
    an optical system configured to selectively illuminate the target structure with radiation and collect at least zero order radiation scattered by the target structure;
    a detector configured to detect an angle-resolved scatter spectrum of the target structure using the zero order radiation; and
    a processor configured to derive a parameter of the lithographic process using asymmetry of the angle-resolved scatter spectrum of the target structure.

14. A lithographic system comprising:
    a lithographic apparatus for use in a lithographic process; and
    a metrology apparatus comprising:
    a support configured to support a substrate on which a target structure comprising first and second targets has been formed, each of the first and second targets comprising a two-dimensional periodic structure formed in a single material layer on the substrate using the lithographic process, wherein the lithographic process comprises defining features of grid elements in the first and second targets, modifying the features defined in the first target by removing portions of each grid element in the first target at predefined locations in the first target, each removed portion being offset from a grid element by a first bias amount that is close to one half of a spatial period of the features, and modifying the features defined in the second target by removing portions of each grid element in the second target at predefined locations in the second target, each removed portion from the second target being offset from a grid element by a second bias amount that is close to one half of the spatial period and different from the first bias amount an optical system configured to selectively illuminate the target structure with radiation and collect at least zero order radiation scattered by the target structure;

a detector configured to detect an angle-resolved scatter spectrum of the target structure using the zero order radiation; and a processor configured to derive a parameter of the lithographic process using asymmetry of the angle-resolved scatter spectrum of the target structure, wherein the metrology apparatus is configured to measure the parameter of the lithographic process using the target structure formed at least partially using the lithographic apparatus.

15. A non-transitory computer program product comprising machine readable instructions which, when run on a suitable processor, cause the processor to perform operations comprising:

illuminating, using an optical system, a target structure with radiation, the target structure comprising first and second targets, each of the first and second targets comprising a two-dimensional periodic structure formed in a single material layer on a substrate using a lithographic process, wherein the lithographic process comprises defining features of grid elements in the first and second targets, modifying the features defined in the first target by removing portions of each grid element in the first target at predefined locations in the first target, each removed portion is offset from a grid element by a first bias amount that is close to one half of a spatial period of the features, and modifying the features defined in the second target by removing portions of each grid element in the second target at predefined locations in the second target, each removed portion from the second target is offset from a grid element by a second bias amount that is close to one half of the spatial period and different from the first bias amount;

obtaining, using a detector, an angle-resolved scatter spectrum of the target structure; and deriving, using the processor, a measurement of a parameter using asymmetry found in the angle-resolved scatter spectrum of the target structure.

16. The non-transitory computer program product according to claim 15, further comprising:

machine readable instructions for controlling a metrology apparatus to illuminate the target structure with the radiation; and machine readable instructions for detecting the angle-resolved scatter spectrum for use in the deriving.

* * * * *